US008404737B2

(12) United States Patent
Liu

(10) Patent No.: US 8,404,737 B2
(45) Date of Patent: *Mar. 26, 2013

(54) SUBSTITUTED ISOINDOLINE-1,3-DIONE DERIVATIVES

(75) Inventor: Julie F. Liu, Lexington, MA (US)

(73) Assignee: Concert Pharmaceuticals, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/364,724

(22) Filed: Feb. 2, 2012

(65) Prior Publication Data

US 2012/0252864 A1 Oct. 4, 2012

Related U.S. Application Data

(63) Continuation of application No. 12/816,295, filed on Jun. 15, 2010, now Pat. No. 8,124,646.

(60) Provisional application No. 61/268,953, filed on Jun. 18, 2009.

(51) Int. Cl.
| | | |
|---|---|---|
| *A61K 31/404* | (2006.01) | |
| *A61P 9/10* | (2006.01) | |
| *A61P 33/06* | (2006.01) | |
| *A61P 31/04* | (2006.01) | |
| *A61P 17/06* | (2006.01) | |
| *A61P 19/04* | (2006.01) | |
| *A61P 27/02* | (2006.01) | |
| *A61P 9/04* | (2006.01) | |
| *A61P 37/06* | (2006.01) | |
| *A61P 35/00* | (2006.01) | |
| *A61P 37/00* | (2006.01) | |
| *A61P 29/00* | (2006.01) | |
| *A61P 19/02* | (2006.01) | |
| *A61P 1/00* | (2006.01) | |
| *A61P 1/04* | (2006.01) | |
| *A61P 25/00* | (2006.01) | |
| *A61P 11/06* | (2006.01) | |
| *A61P 11/00* | (2006.01) | |
| *A61P 31/00* | (2006.01) | |

(52) U.S. Cl. ...................................... 514/417

(58) Field of Classification Search ........................ None
See application file for complete search history.

(56) References Cited

U.S. PATENT DOCUMENTS

| | | |
|---|---|---|
| 6,221,335 B1 | 4/2001 | Foster |
| 6,440,710 B1 | 8/2002 | Keinan et al. |
| 6,603,008 B1 | 8/2003 | Ando et al. |
| 7,517,990 B2 | 4/2009 | Ito et al. |
| 8,124,646 B2 | 2/2012 | Liu |
| 2007/0082929 A1 | 4/2007 | Gant et al. |
| 2007/0197695 A1 | 8/2007 | Potyen et al. |
| 2008/0103122 A1 | 5/2008 | Veltri |

FOREIGN PATENT DOCUMENTS

| | | |
|---|---|---|
| AU | 2006/200 033 A1 | 2/2006 |
| WO | WO-95/26325 A2 | 10/1995 |
| WO | WO-2006/025991 A2 | 3/2006 |
| WO | WO-2007/118651 A1 | 10/2007 |

OTHER PUBLICATIONS

Lagente et al., Mem Inst Oswaldo Cruz, vol. 100, 2004, 131-136.*
Sarcoidosis, Baughman et al., abstract, Am J Respir Crit Care Med, 183, 2011.*
PrurigoNodularis, 2012, C:\Users\sloewe\AppData\Local\Microsoft\Windows\Temporary Internet Files\Content.Outlook\RBA6DCI9\NCT00869089-prurigo nodularis htm.htm.*
Behcet, 2012, C:\Users\sloewe\AppData\Local\Microsoft\Windows\Temporary Internet Files\Content.Outlook\RBA6DCI9\NCT00866359—Behcet's Disease htm.htm.*
Lupus, 2012, C:\Users\sloewe\AppData\Local\Microsoft Windows\Temporary Internet Files\Content.Outlook\RBA6DCI9\NCT00708916-lupus htm.htm.*
AnkylosingSpondylitis, 2012, C:\Users\sloewe\AppData\Local\Microsoft\Windows\Temporary Internet Files\Content.Outlook\RBA6DCI9\NCT00708916-lupus htm.htm.*
RheumatoidArthritis, 2012, C:\Users\sloewe\AppData\Local\Microsoft\Windows\Temporary Internet Files\Content.Outlook\RBA6DC19\NCT01250548-rheumatoid arthritis htm.htm.*
Baillie, "The Use of Stable Isotopes in Pharmacological Research", Pharmacological Reviews, vol. 33, No. 2, pp. 81-132 (1981).
Baumer et al., "Highly Selective Phosphodiesterase 4 Inhibitors for the Treatment of Allergic Skin Disease and Psoriasis," Inflammation & Allergy—Drug Targets, 6:17-26 (2006).
Browne, "Stable Isotope Techniques in Early Drug Development: An Economic Evaluation", J. Clin. Pharmacol, vol. 38, pp. 213-220 (1998).
Cherrah, et al., "Study of Deuterium Isotope Effects on Protein Binding by Gas Chromatography/Mass Spectrometry. Caffeine and Deuterated Isotopomers", Biomedical and Environmental Mass SQectrometry, vol. 14, pp. 653-657 (1987).
Dyck, et al., "Effects of Deuterium Substitution on the Catabolism of .B-Phenylethylamine: An In Vivo Study", Journal of Neurochemistry, vol. 46, No. 2, pp. 399-404 (1986).
Fisher, et al., "The complexities inherent in attempts to decrease drug clearance by blocking sites of CYP-mediated metabolism", Current Opinion in Drug Discovery Development, vol. 9, No. 1, pp. 101-109 (2006).
Foster, "Deuterium isotope effects in studies of drug metabolism", TIPS, pp. 524-527 (1984).
Foster, "Deuterium isotope effects in the metabolism of drugs and xenobiotics", Advances in Drug Research vol. 14, pp. 2-40 (1985).

(Continued)

*Primary Examiner* — Sun Jae Loewe
(74) *Attorney, Agent, or Firm* — McCarter & English LLP; Steven G. Davis

(57) ABSTRACT

This invention relates to novel substituted isoindoline-1,3-dione derivatives and pharmaceutically acceptable salts thereof. More specifically, the invention relates to novel substituted isoindoline-1,3-dione derivatives that are analogues of apremilast. This invention also provides compositions comprising a compound of this invention and a carrier and the use of disclosed compounds and compositions in methods of treating diseases and conditions that are beneficially treated by administering apremilast.

21 Claims, No Drawings

OTHER PUBLICATIONS

Gouyetie, et al., "Synthesis of Deuterium-labelled Elliptinium and its Use in Metabolic Studies", Biomedical and Environmental Mass Spectrometry, vol. 15, pp. 243-247 (1988).

Haskins, "The Application of Stable Isotopes in Biomedical Research", Biomedical Mass Spectrometry, vol. 9, No. 7, pp. 269-277 (1982).

Honma, et al., "Liberation of Deuterium from the Piperidine Ring during Hydroxylation", Drug Metabolism and Disposition, vol. 15, No. 4, pp. 551-559 (1987).

Kushner, et al., "Pharmacological uses and perspectives of heavy water and deuterated compounds", Can J Physiol. Pharmacol., vol. 77, pp. 79-88 (1999).

Man et al., "Discovery of (S)-N-{2-{1-(3-Ethoxy-4-methoxyphenyl)-2-methanesulfonylethyl-1,3-dioxo-2,3-dihydro-1H-isoindol-4-yl}acetamide (Apremilast), a Potent and Orally Active Phosphodiesterase 4 and Tumor Necrosis Factor-a Inhibitor," J.Med. Chem. 52:1522-1524 (2009).

Matsubara, et al., "Pharmacokinetics and Disposition of Silodosin (KMD-3213)", Yakugaku Zasshi, vol. 126, pp. 237-245 (2006).

Park et al., "Metabolism of Fluorine-Containing Drugs," Annu. Rev. Pharmacol. Toxicol. 41:443-470 (2001).

PCT International Search Report and Written Opinion—(PCT/US201 01038577), mailed Aug. 30, 2010 (16 pages).

Pieniaszek, et al., "Moricizine Bioavailablity via Simultaneous, Dual, Stable Isotope Administration: Bioequivalence Implications", The Journal of Clinical Pharmacology, vol. 39, pp. 817-825 (1999).

Tonn, et al., "Simultaneous Analysis of Diphenhydramine and a Stable Isotope Analog (2H10)Diphenhydramine Using Capillary Gas Chromatography with Mass Selective Detection in Biological Fluids from Chronically Instrumented Pregnant Ewes", Biological Mass Spectrometry, vol. 22, pp. 633-642 (1993).

Walen, "The Application of Stable Isotopes to Studies of Drug Bioabailablity and Bioequivalence", The Journal of Clinical Pharmacology, vol. 26, pp. 419-424 (1986).

* cited by examiner

SUBSTITUTED ISOINDOLINE-1,3-DIONE DERIVATIVES

RELATED APPLICATIONS

This application is a continuation of U.S. application Ser. No. 12/816,295, filed on Jun. 15, 2010 (now U.S. Pat. No. 8,124,646), which claims the benefit of U.S. Provisional Application Ser. No. 61/268,953, filed on Jun. 18, 2009. These prior applications are incorporated herein by reference in their entirety.

BACKGROUND OF THE INVENTION

Many current medicines suffer from poor absorption, distribution, metabolism and/or excretion (ADME) properties that prevent their wider use or limit their use in certain indications. Poor ADME properties are also a major reason for the failure of drug candidates in clinical trials. While formulation technologies and prodrug strategies can be employed in some cases to improve certain ADME properties, these approaches often fail to address the underlying ADME problems that exist for many drugs and drug candidates. One such problem is rapid metabolism that causes a number of drugs, which otherwise would be highly effective in treating a disease, to be cleared too rapidly from the body. A possible solution to rapid drug clearance is frequent or high dosing to attain a sufficiently high plasma level of drug. This, however, introduces a number of potential treatment problems such as poor patient compliance with the dosing regimen, side effects that become more acute with higher doses, and increased cost of treatment. A rapidly metabolized drug may also expose patients to undesirable toxic or reactive metabolites.

Another ADME limitation that affects many medicines is the formation of toxic or biologically reactive metabolites. As a result, some patients receiving the drug may experience toxicities, or the safe dosing of such drugs may be limited such that patients receive a suboptimal amount of the active agent. In certain cases, modifying dosing intervals or formulation approaches can help to reduce clinical adverse effects, but often the formation of such undesirable metabolites is intrinsic to the metabolism of the compound.

In some select cases, a metabolic inhibitor will be co-administered with a drug that is cleared too rapidly. Such is the case with the protease inhibitor class of drugs that are used to treat HIV infection. The FDA recommends that these drugs be co-dosed with ritonavir, an inhibitor of cytochrome P450 enzyme 3A4 (CYP3A4), the enzyme typically responsible for their metabolism (see Kempf, D. J. et al. Antimicrobial agents and chemotherapy, 1997, 41(3): 654-60). Ritonavir, however, causes adverse effects and adds to the pill burden for HIV patients who must already take a combination of different drugs. Similarly, the CYP2D6 inhibitor quinidine has been added to dextromethorphan for the purpose of reducing rapid CYP2D6 metabolism of dextromethorphan in a treatment of pseudobulbar affect. Quinidine, however, has unwanted side effects that greatly limit its use in potential combination therapy (see Wang, I. et al., Clinical Pharmacology and Therapeutics, 1994, 56(6 Pt 1): 659-67; and FDA label for quinidine at www.accessdata.fda.gov).

In general, combining drugs with cytochrome P450 inhibitors is not a satisfactory strategy for decreasing drug clearance. The inhibition of a CYP enzyme's activity can affect the metabolism and clearance of other drugs metabolized by that same enzyme. CYP inhibition can cause other drugs to accumulate in the body to toxic levels.

A potentially attractive strategy for improving a drug's metabolic properties is deuterium modification. In this approach, one attempts to slow the CYP-mediated metabolism of a drug or to reduce the formation of undesirable metabolites by replacing one or more hydrogen atoms with deuterium atoms. Deuterium is a safe, stable, non-radioactive isotope of hydrogen. Compared to hydrogen, deuterium forms stronger bonds with carbon. In select cases, the increased bond strength imparted by deuterium can positively impact the ADME properties of a drug, creating the potential for improved drug efficacy, safety, and/or tolerability. At the same time, because the size and shape of deuterium are essentially identical to those of hydrogen, replacement of hydrogen by deuterium would not be expected to affect the biochemical potency and selectivity of the drug as compared to the original chemical entity that contains only hydrogen.

Over the past 35 years, the effects of deuterium substitution on the rate of metabolism have been reported for a very small percentage of approved drugs (see, e.g., Blake, M J et al, J Pharm Sci, 1975, 64:367-91; Foster, A B, Adv Drug Res 1985, 14:1-40 ("Foster"); Kushner, D J et al, Can J Physiol Pharmacol 1999, 79-88; Fisher, M B et al, Curr Opin Drug Discov Devel, 2006, 9:101-09 ("Fisher")). The results have been variable and unpredictable. For some compounds deuteration caused decreased metabolic clearance in vivo. For others, there was no change in metabolism. Still others demonstrated increased metabolic clearance. The variability in deuterium effects has also led experts to question or dismiss deuterium modification as a viable drug design strategy for inhibiting adverse metabolism (see Foster at p. 35 and Fisher at p. 101).

The effects of deuterium modification on a drug's metabolic properties are not predictable even when deuterium atoms are incorporated at known sites of metabolism. Only by actually preparing and testing a deuterated drug can one determine if and how the rate of metabolism will differ from that of its non-deuterated counterpart. See, for example, Fukuto et al. (J. Med. Chem. 1991, 34, 2871-76). Many drugs have multiple sites where metabolism is possible. The site(s) where deuterium substitution is required and the extent of deuteration necessary to see an effect on metabolism, if any, will be different for each drug.

Apremilast, also known as (+)-N-[2-[1(S)-(3-Ethoxy-4-methoxyphenyl)-2-(methylsulfonyl)ethyl]-1,3-dioxo-2,3-dihydro-1H-isoindol-4-yl]acetamide, is a PDE4 inhibitor and also acts to reduce TNF-α levels. Apremilast is in clinical trials for the treatment of psoriasis, plaque-type psoriasis, refractory psoriasis, cutaneous sarcoidosis, psoriatic arthritis, Behçet's Disease, prurigo nodularis, cutaneous lupus, and uveitis, among others.

Common adverse events associated with PDE4 inhibitors generally include headache, nausea, emesis and gastrointestinal disturbances.

It would be desirable to provide a compound that has the beneficial activities of apremilast and other benefits, e.g., reduced adverse side effects, with a decreased metabolic liability, to further extend its pharmacological effective life, enhance patient compliance and, potentially, to decrease population pharmacokinetic variability and/or decrease its potential for dangerous drug-drug interactions.

SUMMARY OF THE INVENTION

This invention relates to novel substituted isoindoline-1,3-dione derivatives and pharmaceutically acceptable salts thereof.

More specifically, the invention relates to novel substituted isoindoline-1,3-dione derivatives that are analogues of apremilast. This invention also provides compositions comprising a compound of this invention and a carrier and the use of disclosed compounds and compositions in methods of treating diseases and conditions that are beneficially treated by administering apremilast.

DETAILED DESCRIPTION OF THE INVENTION

The term "treat" means decrease, suppress, attenuate, diminish, arrest, or stabilize the development or progression of a disease (e.g., a disease or disorder delineated herein), lessen the severity of the disease or improve the symptoms associated with the disease.

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of apremilast will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada E et al., Seikagaku 1994, 66:15; Gannes L Z et al., Comp Biochem Physiol Mot Integr Physiol 1998, 119:725.

In the compounds or this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

The term "isotopic enrichment factor" as used herein means the ratio between the isotopic abundance and the natural abundance of a specified isotope.

In other embodiments, a compound of this invention has an isotopic enrichment factor for each designated deuterium atom or at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The term "isotopologue" refers to a species in which the chemical structure differs from a specific compound of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

The invention also provides salts of the compounds of the invention.

A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsullonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The pharmaceutically acceptable salt may also be a salt of a compound of the present invention having an acidic functional group, such as a carboxylic acid functional group, and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

The compounds of the present invention (e.g., compounds of Formula I), may contain an asymmetric carbon atom, for example, as the result of deuterium substitution or otherwise. As such, compounds of this invention can exist as either individual enantiomers, or mixtures of the two enantiomers. Accordingly, a compound of the present invention may exist as either a racemic mixture or a scalemic mixture, such as a mixture containing predominantly one stereoisomer, or as individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers are present. Methods of obtaining or synthesizing an individual enantiomer for a given compound are known in the art and may be applied as practicable to final compounds or to starting material or intermediates.

Unless otherwise indicated, when a disclosed compound is named or depicted by a structure without specifying the stereochemistry and has one or more chiral centers, it is understood to represent all possible stereoisomers of the compound.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" and "d" both refer to deuterium. "Stereoisomer" refers to both enantiomers and diastereomers. "Tert" and "t-" each refer to tertiary. "US" refers to the United States of America.

"Substituted with deuterium" refers to the replacement of one or more hydrogen atoms with a corresponding number of deuterium atoms.

Throughout this specification, a variable may be referred to generally (e.g., "each R") or may be referred to specifically (e.g., $R^1$, $R^2$, $R^3$, etc.). Unless otherwise indicated, when a variable is referred to generally, it is meant to include all specific embodiments of that particular variable.

Therapeutic Compounds

The present invention provides a compound of Formula I:

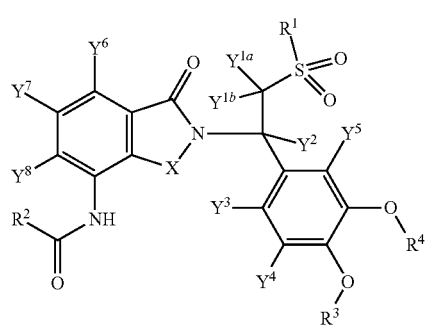

Formula I or a pharmaceutically acceptable salt thereof, wherein:
$R^1$ is selected from $CH_3$, $CH_2D$, $CHD_2$, and $CD_3$;
$R^2$ is selected from the group consisting of methyl, isopropyl, cyclopentyl, cyclopropyl, 2-furanyl, trifluoromethyl, methoxymethyl, aminomethyl, dimethylaminomethyl, dimethylamino-1-ethyl, 1-dimethylamino-ethyl, and 2-dimethylamino-ethyl, wherein $R^2$ is optionally substituted with deuterium;
$R^3$ is selected from $CH_3$, $CH_2D$, $CHD_2$, $CD_3$, $CF_3$, $CHF_2$, $CH_2F$, $CDF_2$, and $CD_2F$;
$R^4$ is an ethyl group substituted with zero to five deuterium, or is a cyclopentyl group substituted with zero to nine deuterium;
X is selected from $CH_2$, CHD, $CD_2$, and C=O;
each of $Y^{1a}$, $Y^{1b}$, $Y^2$, $Y^3$, $Y^4$, $Y^5$, $Y^7$ and $Y^8$ is independently selected from H and D; and
$Y^6$ is selected from Cl, H, and D;
provided that if $R^1$ is $CH_3$; $R^2$ is not substituted with deuterium; $R^3$ is $CH_3$, $CF_3$, $CHF_2$, or $CH_2F$; $R^4$ is an ethyl group not substituted with deuterium or a cyclopentyl group not substituted with deuterium; X is $CH_2$ or C=O; and $Y^6$ is Cl or H; then at least one of $Y^{1a}$, $Y^{1b}$, $Y^2$, $Y^3$, $Y^4$, $Y^5$, $Y^7$ and $Y^8$ is D.

In one embodiment, the compound of Formula I is a compound of Formula II:

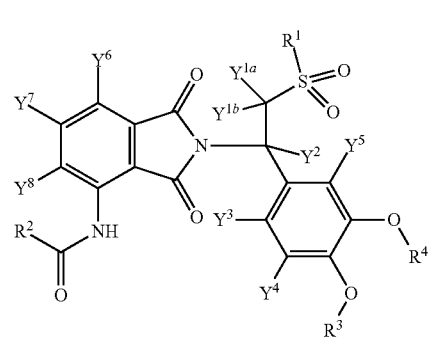

Formula II or a pharmaceutically acceptable salt thereof, wherein:
$R^1$ is selected from $CH_3$ and $CD_3$;
$R^2$ is selected from the group consisting of methyl, isopropyl, cyclopentyl, cyclopropyl, 2-furanyl, trifluoromethyl, methoxymethyl, aminomethyl, dimethylaminomethyl, dimethylamino-1-ethyl, 1-dimethylamino-ethyl, and 2-dimethylamino-ethyl, wherein $R^2$ is optionally substituted with deuterium;
$R^3$ is selected from $CH_3$, $CD_3$, $CF_3$, $CHF_2$, $CH_2F$, $CDF_2$, and $CD_2F$;
$R^4$ is selected from $CH_2CH_3$, $CD_2CD_3$, $CD_2CH_3$, and $CH_2CD_3$; and
each Y is independently selected from H and D;
provided that if $R^1$ is $CH_3$; $R^2$ is not substituted with deuterium; $R^3$ is $CH_3$, $CF_3$, $CHF_2$, or $CH_2F$; and $R^4$ is $CH_2CH_3$; then at least one Y is D.

In one embodiment of Formula I or Formula II, $R^1$ is $CH_3$ or $CD_3$.

In one embodiment of Formula I or Formula II, $R^2$ is $CH_3$ or $CD_3$.

In one embodiment of Formula I or Formula II, $R^3$ is $CH_3$ or $CD_3$.

In one embodiment of Formula I or Formula II, $Y^6$, $Y^7$ and $Y^8$ are the same. In one aspect, $Y^6$, $Y^7$ and $Y^8$ are each hydrogen.

In one embodiment of Formula I or Formula II, $Y^{1a}$ and $Y^{1b}$ are the same. In one aspect, $Y^{1a}$ and $Y^{1b}$ are both hydrogen. In another aspect, $Y^{1a}$ and $Y^{1b}$ are both deuterium.

In one embodiment of Formula I or Formula II, $Y^3$, $Y^4$ and $Y^5$ are the same. In one aspect, $Y^3$, $Y^4$ and $Y^5$ are each hydrogen.

In one embodiment of Formula I or Formula II, $R^4$ is $CD_2CD_3$. In one embodiment of Formula I or Formula II, $R^2$ is $CH_3$ or $CD_3$; $R^3$ is $CH_3$ or $CD_3$; $Y^6$, $Y^7$ and $Y^8$ are the same; $Y^{1a}$ and $Y^{1b}$ are the same; and $Y^3$, $Y^4$ and $Y^5$ are the same.

In one embodiment of Formula I or Formula II, $R^1$ is $CH_3$ or $CD_3$; $R^2$ is $CH_3$ or $CD_3$; $R^3$ is $CH_3$ or $CD_3$; $R^4$ is $CD_2CD_3$; $Y^6$, $Y^7$ and $Y^8$ are the same; $Y^{1a}$ and $Y^{1b}$ are the same; and $Y^3$, $Y^4$ and $Y^5$ are the same.

In one embodiment, the compound of Formula I is a compound of Formula Ia, having predominantly the (S) configuration at the carbon attached to $Y^2$;

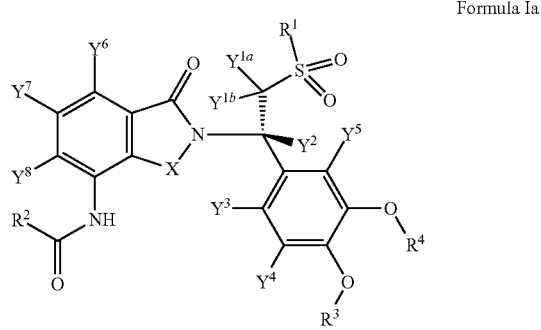

Formula Ia or a pharmaceutically acceptable salt thereof, wherein the remaining variables are as defined for Formula I.

In one embodiment, the compound of Formula Ia is substantially free of other stereoisomers.

In one embodiment, the compound of Formula I is a compound of Formula Ib, having predominantly the (R) configuration at the carbon attached to $Y^2$:

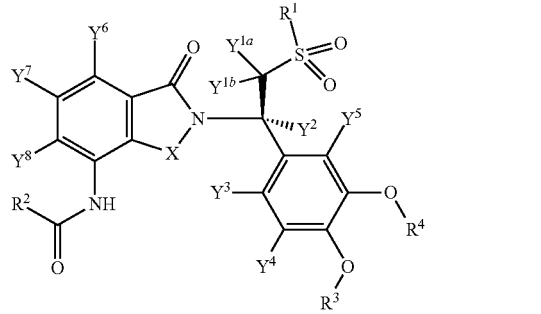

Formula Ib or a pharmaceutically acceptable salt thereof, wherein the remaining variables are as defined for Formula I.

In one embodiment, the compound of Formula Ib is substantially free of other stereoisomers.

In one embodiment of Formula Ia or Formula Ib, $R^1$ is $CH_3$ or $CD_3$.

In one embodiment of Formula Ia or Formula Ib, $R^2$ is $CH_3$ or $CD_3$.

In one embodiment of Formula Ia or Formula Ib, $R^3$ is $CH_3$ or $CD_3$.

In one embodiment of Formula Ia or Formula Ib, $Y^6$, $Y^7$ and $Y^8$ are the same. In one aspect, $Y^6$, $Y^7$ and $Y^8$ are each hydrogen.

In one embodiment of Formula Ia or Formula Ib, $Y^{1a}$ and $Y^{1b}$ are the same. In one aspect, $Y^{1a}$ and $Y^{1b}$ are both hydrogen. In another aspect, $Y^{1a}$ and $Y^{1b}$ are both deuterium.

In one embodiment of Formula Ia or Formula Ib, $Y^3$, $Y^4$ and $Y^5$ are the same. In one aspect, $Y^3$, $Y^4$ and $Y^5$ are each hydrogen.

In one embodiment of Formula Ia or Formula Ib, $R^4$ is $CD_2CD_3$.

In one embodiment of Formula Ia or Formula Ib, $R^1$ is $CH_3$ or $CD_3$; $R^2$ is $CH_3$ or $CD_3$; $R^3$ is $CH_3$ or $CD_3$; $R^4$ is $CD_2CD_3$; $Y^6$, $Y^7$ and $Y^8$ are the same; $Y^{1a}$ and $Y^{1b}$ are the same; and $Y^3$, $Y^4$ and $Y^5$ are the same.

In one embodiment, the compound of Formula I is selected from the group consisting of:

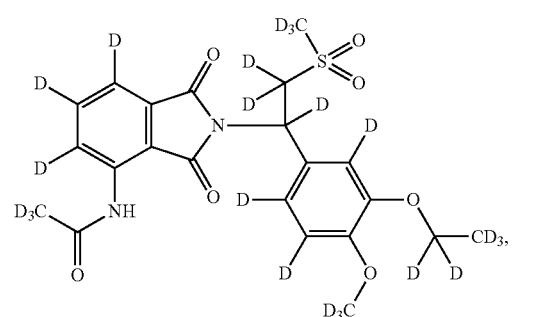

Compound 100

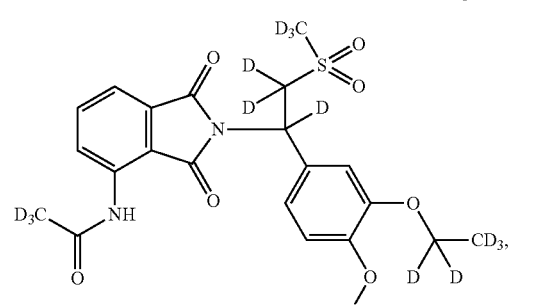

Compound 101

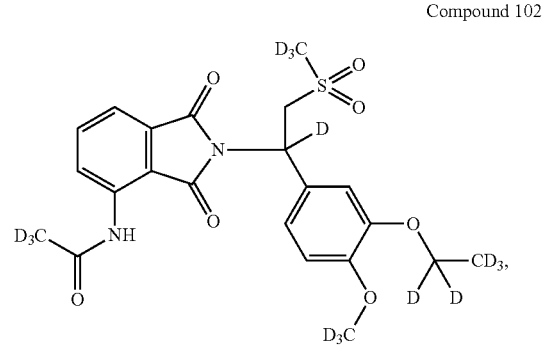

Compound 102

Compound 103
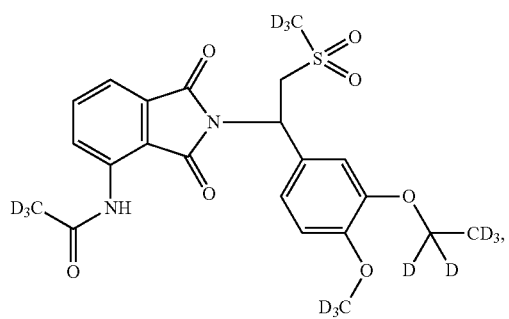
Compound 104
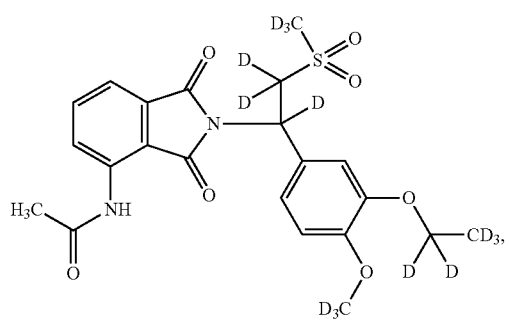
Compound 105
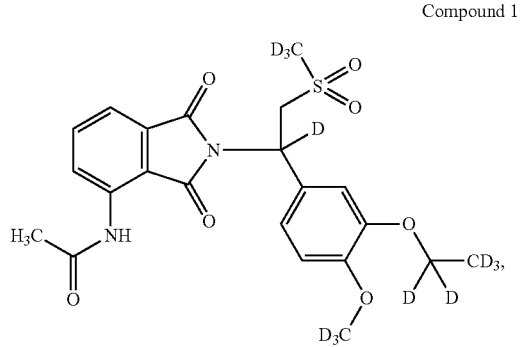
Compound 106
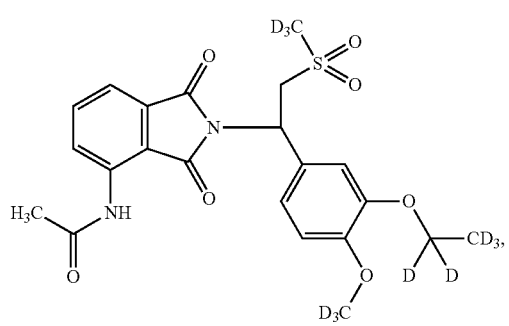
Compound 107
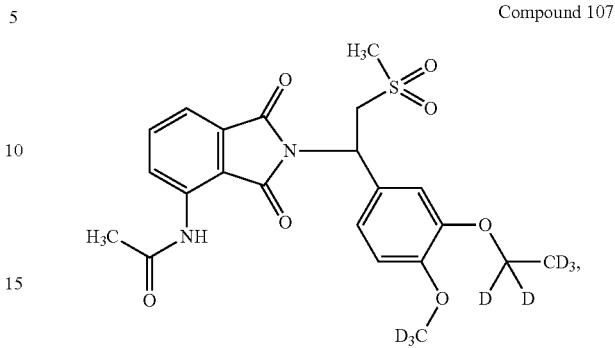
Compound 108
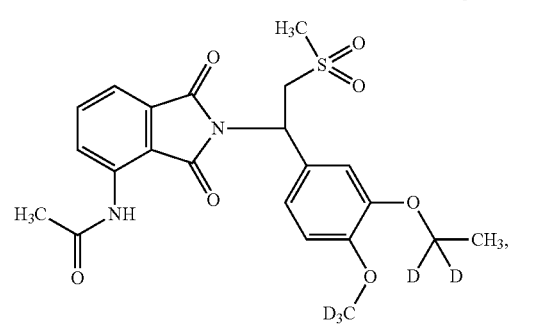
Compound 109
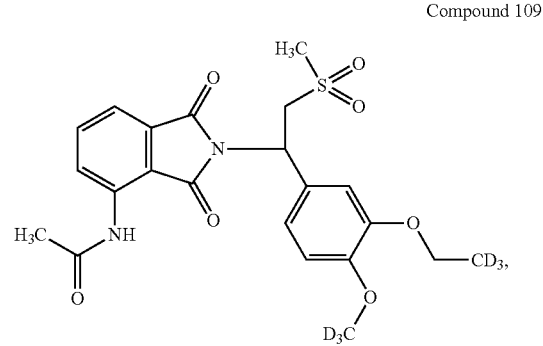
Compound 110
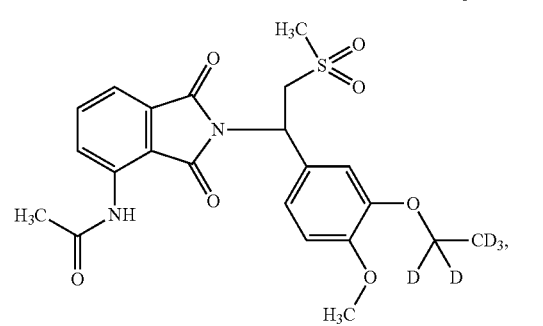

Compound 111

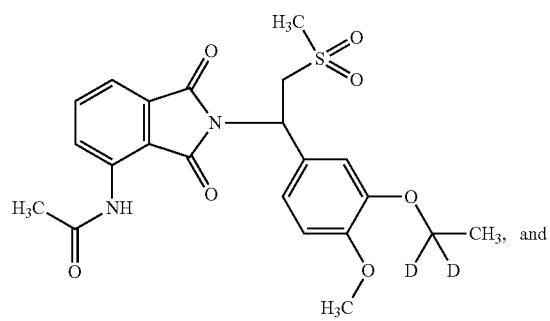

and

Compound 112

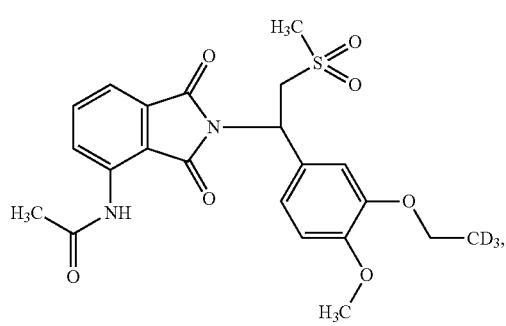

or a pharmaceutically acceptable salt of any of the foregoing.

In one embodiment, the compound of Formula I is selected from the group consisting of:

Compound 113

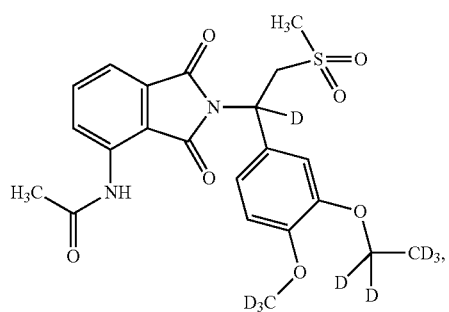

Compound 114

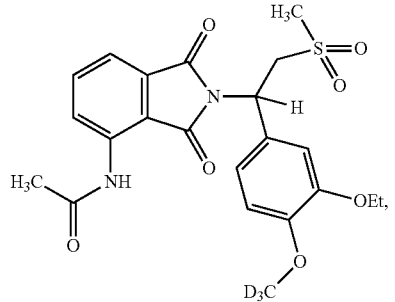

Compound 115

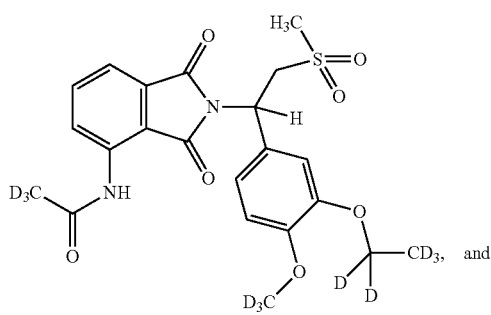

and

Compound 116

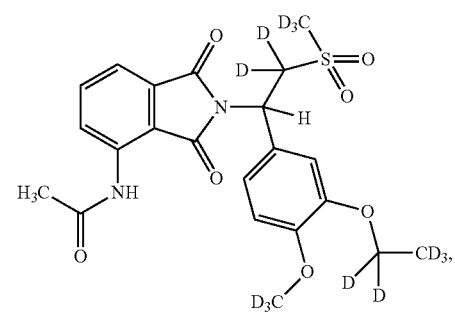

or a pharmaceutically acceptable salt of any of the foregoing.

In one embodiment, the compound is a compound of Formula Ia and is selected from the group consisting of:

Compound 107a

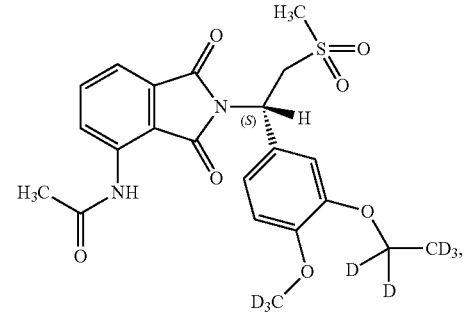

Compound 110a

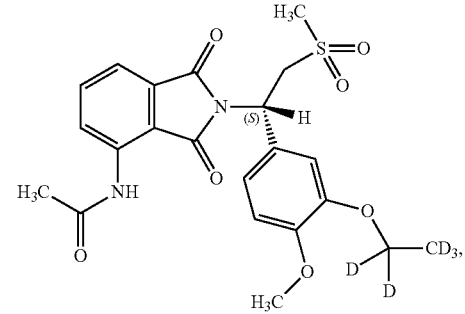

-continued

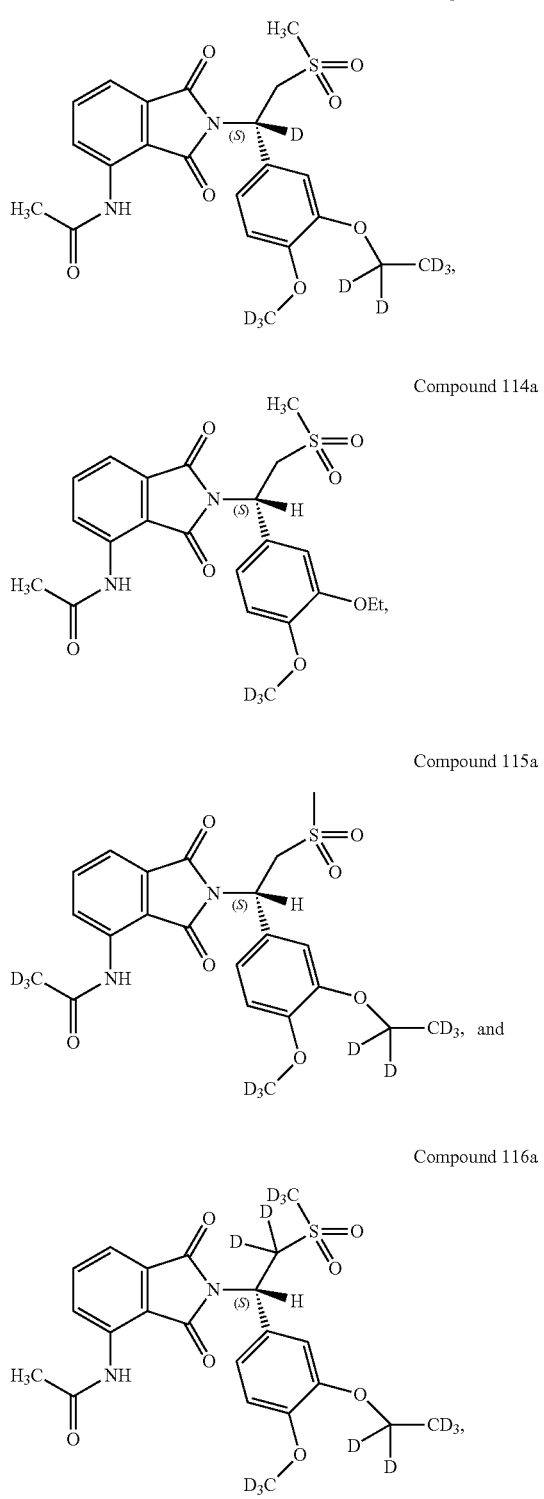

Compound 113a

Compound 114a

Compound 115a

Compound 116a or a pharmaceutically acceptable salt of any of the foregoing.

One embodiment provides a compound that is predominantly the (S) enantiomer of compound 100, 101, 102, 103, 104, 105, 106, 107, 108, 109, 110, 111, or 112 or a pharmaceutically acceptable salt of any of the foregoing.

One embodiment provides a compound that is predominantly the (S) enantiomer of compound 113, 114, 115, 116 or a pharmaceutically acceptable salt of any of the foregoing.

One embodiment provides a compound that is predominantly the (R) enantiomer of compound 100, 101, 102, 103, 104, 105, 106, 107, 108, 109, 110, 111, or 112 or a pharmaceutically acceptable salt of any of the foregoing.

One embodiment provides a compound that is predominantly the (R) enantiomer of compound 113, 114, 115, 116 or a pharmaceutically acceptable salt of any of the foregoing.

In another set of embodiments, any atom not designated as deuterium in any of the embodiments set forth above for a compound of Formula I, I(a), or I(b) is present at its natural isotopic abundance.

The synthesis of compounds of Formula I can be readily achieved by synthetic chemists of ordinary skill. Relevant procedures and intermediates are disclosed, for instance in Man, H. W. et al., Journal of Medicinal Chemistry (2009), 52(6), 1522-1524; Muller, G. W. et al. Journal of Medicinal Chemistry (1996), 39(17), 3238-3240; WO2006/025991; AU2006/200033; WO2001/034606; U.S. Pat. No. 6,020,358; and U.S. Pat. No. 6,667,316.

Such methods can be carried out utilizing corresponding demented and optionally, other isotope-containing reagents and/or intermediates to synthesize the compounds delineated herein, or invoking standard synthetic protocols known in the art for introducing isotopic atoms to a chemical structure. Certain intermediates can be used with or without purification (e.g., filtration, distillation, sublimation, crystallization, trituration, solid phase extraction, and chromatography).

EXEMPLARY SYNTHESIS

Scheme 1: General Route to Compounds of Formula I.

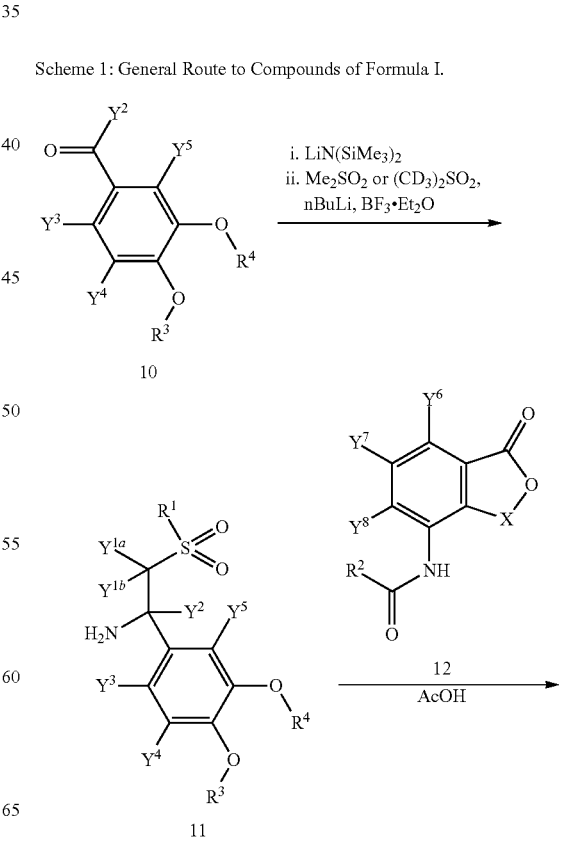

-continued

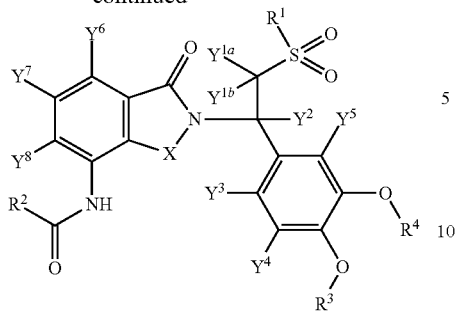

Formula I

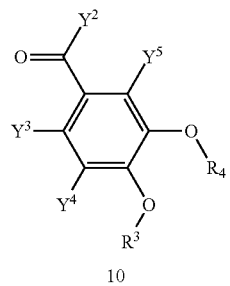

Scheme 1 depicts a general route to preparing compounds of Formula I, according to the general methods of Man, H W; et al. Journal of Medicinal Chemistry (2009), 52(6), 1522-1524. Thus, appropriately substituted aldehyde 10 is treated with lithium hexamethyldisilazide, followed by lithium dimethylsulfone and boron trifluoride etherate to afford racemic amine 11, which has a stereocenter at the carbon attached to $Y^2$. If desired, racemic amine 11 may be resolved via treatment with an enantiopure acid in methanol. For example, treatment of racemic amine 11 with N-acetyl-L-leucine affords amine 11 as the S enantiomer, while treatment N-acetyl-D-leucine affords amine 11 as the R enantiomer. Amine 11 may be used as the racemate, as the S enantiomer, or as the R enantiomer to yield compounds of Formula I upon treatment with anhydride 12 either neat or in a solvent such as acetic acid. One skilled in the art will appreciate that the use of appropriately deuterated intermediates and reagents in Scheme 1 results in the production of compounds of Formula I bearing various patterns of deuterium substitution.

Scheme 2: Preparation of aldehyde 10.

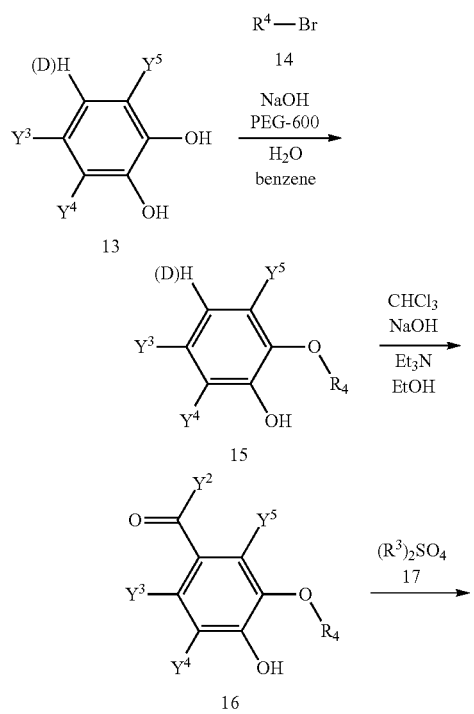

Scheme 2 depicts a preparation of aldehyde 10, which is a useful starting material for Scheme 1. As generally described in Li, Juren; et al. Hecheng Huaxue (1993), 1(4), 333-40, appropriately-deuterated diol 13 is treated with appropriately-deuterated ethyl bromide 14 under phase transfer conditions to afford phenol 15. Reimer-Tiemann reaction of phenol 15 with chloroform provides aldehyde 16. Deuterated reagents and solvents may be useful in this step to maximize levels of isotopic incorporation. Alternatively, the tetrabutylammonium bromide conditions generally described by Li, Ying-chun; et al. Yingyong Fluagong (2004), 33(1), 26-27 may be used to convert 15 to 16. According to the general methods of Kiehlmann, E.; et al., Organic Preparations and Procedures International (1982), 14(5), 337-42, treatment of 16 with appropriately-deuterated dimethylsulfate 17 provides desired intermediate 10.

For example, commercially-available dimethyl-d6 sulfite may be used as reagent 17 in Scheme 2 to ultimately produce compounds of Formula I wherein $R^3$ is $CD_3$. In another example, commercially-available bromoethane-d5 may be used as reagent 14 in Scheme 2 to ultimately produce compounds of Formula I wherein $R^4$ is $-CD_2CD_3$. Similarly, commercially-available bromoethane-2,2,2-d3 and bromoethane-1,1-d2 would also be of use in Scheme 2 to ultimately produce compounds of Formula I bearing various other patterns of deuterium substitution at $R^4$.

Scheme 3. Preparation of intermediates 12a and 12b.

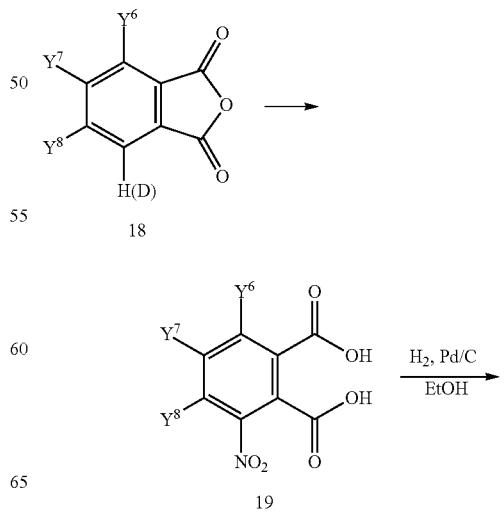

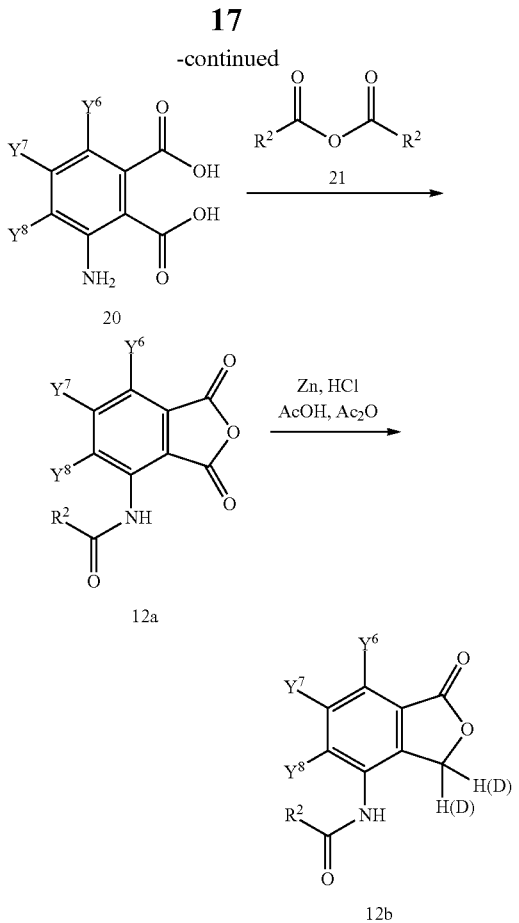

Scheme 3 depicts a preparation of intermediate 12a, an example of intermediate 12 wherein X is C=O, and intermediate 12b, an example of intermediate 12 wherein X is $CH_2$, $CHD_2$ or $CD_2$. Nitration of anhydride scaffold 18 is well known in the literature, for example in patent applications WO 2005051870, CN 1740138, and CN 1405143; and in literature articles including Chen, Zhi-min; et al. Hecheng Huaxue (2004), 12(2), 167-169, 173; Zhu, Zhi-jia; et al. Huaxue Shiji (2003); 25(5), 306, 308; Ma, S. L.; et al. Polish Journal of Chemistry (2002), 76(4), 511-517; and Culhane, P. J.; et al. Organic Syntheses (1927), 7, no pp. given. Use of appropriately-deuterated starting materials and reagents will produce deuterated versions of 19. According to the general methods described in US patent application US 2008234359, hydrogenation of 19 in the presence of palladium on carbon affords amine 20, which is then treated with appropriately-deuterated acetic anhydride 21 to provide intermediate 12a. According to the general methods of Wamser, C. C.; et al. J. Org. Chem. (1976), 41 (17), 2929-31, intermediate 12a may be reduced with zinc and acid to provide intermediate 12b. Commercially-available DCl, acetic acid-d4, and acetic anhydride-d6 may be used in the final step to provide alternate patterns of deuterium incorporation.

For example, commercially-available 3-aminophthalic acid may be used in Scheme 3 as intermediate 20 to ultimately produce compounds of Formula I wherein $Y^6$, $Y^7$, and $Y^8$ are all hydrogen. In another example, commercially-available acetic anhydride-d6 may be used in Scheme 3 as reagent 21 to ultimately yield compounds of Formula I wherein $R^2$ is $CD_3$. In yet another example, commercially-available phthalic-d4 anhydride may be used in Scheme 3 as anhydride 18 to ultimately provide compounds of Formula I wherein $Y^6$, $Y^7$, and $Y^8$ are all deuterium.

Combinations of substituents and variables envisioned by this invention are only those that result in the formation of stable compounds.

Compositions

The invention also provides compositions comprising an effective amount of a compound of Formula I (e.g., including any of the formulae herein), or a pharmaceutically acceptable salt of said compound; and an acceptable carrier. The carrier(s) are "acceptable" in the sense of being compatible with the other ingredients of the formulation and, in the case of a pharmaceutically acceptable carrier, not deleterious to the recipient thereof in an amount used in the Medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, Md. (20th ed. 2000).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween; 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the patient therapeutics may be local, so as to be administered at the site of interest. Various techniques can be used for providing the subject compositions at the site of interest, such as injection, use of catheters, trocars, projectiles pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the patient, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent.

The second therapeutic agent may be selected from any compound or therapeutic agent known to have or that demonstrates advantageous properties when administered with a compound having the same mechanism of action as apremilast. Such agents include those indicated as being useful in combination with apremilast, including but not limited to, those agents useful for the treatment of psoriasis, including plaque-type psoriasis and refractory psoriasis; sarcoidosis, including cutaneous sarcoidosis; psoriatic arthritis; Behçet's Disease; prurigo nodularis; lupus, including cutaneous lupus; and uveitis, among others.

In one embodiment, the second therapeutic agent is an agent useful for the treatment of psoriasis or sarcoidosis.

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound oldie present invention is present in an effective amount. As used herein, the term "effective amount" refers to an amount which, when administered in a proper dosing regimen, is sufficient to treat (therapeutically or prophylactically) the target disorder. For example, to reduce the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., Cancer Chemother. Rep, 1966, 50: 219. Body surface area may be approximately determined from height and weight of the patient. See, e.g., Scientific Tables, Geigy Pharmaceuticals, Ardsley, N.Y., 1970, 537.

In one embodiment, an effective amount of a compound of this invention can range from about 0.2 to 2000 mg per treatment. In more specific embodiments the range is from about 2 to 1000 mg or from 4 to 400 mg or most specifically from 20 to 200 mg per treatment. Treatment typically is administered at a rate of between 0.625 to 1.25 ng/kg/min. The infusion rate can be increased in increments of no more than 1.25 ng/kg/min per week for the first four weeks and then no more than 2.5 ng/kg/min per week for the remaining duration of infusion.

Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician. For example, guidance for selecting an effective dose can be determined by reference to the prescribing information for apremilast.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al. eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Taruscon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

In another embodiment, the invention provides a method of inhibiting PDE4 in a subject, comprising administering to the subject a compound of Formula I herein or a pharmaceutically acceptable salt thereof.

In another embodiment, the invention provides a method of reducing TNF-α levels in a subject, comprising administering to the subject a compound of Formula I herein or a pharmaceutically acceptable salt thereof.

According to another embodiment, the invention provides a method of treating a disease that is beneficially treated by apremilast comprising the step of administering to a patient in need thereof an effective amount of a compound of Formula I or a pharmaceutically acceptable salt thereof or a composition of this invention. Such diseases are well known in the art and are disclosed in, but not limited to the following patents and published applications: WO2006/025991; AU2006/200033; WO2001/034606; U.S. Pat. No. 6,020,358; and U.S. Pat. No. 6,667,316.

Such diseases include, but are not limited to, septic shock, sepsis, endotoxic shock, hemodynamic shock and sepsis syndrome, post ischemic reperfusion injury, malaria, mycobacterial infection, meningitis; psoriasis, including plaque-type psoriasis and refractory psoriasis; sarcoidosis, including cutaneous sarcoidosis; psoriatic arthritis; Behçet's Disease; prurigo nodularis; lupus, including cutaneous lupus; uveitis; congestive heart failure, fibrotic disease, cachexia, graft rejection, cancer, autoimmune disease, opportunistic infections in AIDS, rheumatoid arthritis, rheumatoid spondylitis, osteoarthritis, other arthritic conditions, Crohn's disease, ulcerative colitis, multiple sclerosis, systemic lupus erythrematosis, ENL in leprosy, radiation damage, hyperoxic alveolar injury, undesirable angiogenesis, inflammatory disease, arthritis, inflammatory bowel disease, aphthous ulcers, asthma, adult respiratory distress syndrome, and AIDS.

In one particular embodiment, the method of this invention is used to treat psoriasis or sarcoidosis.

Methods delineated herein also include those wherein the patient is identified as in need of a particular stated treatment. Identifying a patient in need of such treatment can be in the judgment of a patient or a health care professional and can be subjective (e.g. opinion) or objective (e.g. measurable by a test or diagnostic method).

In another embodiment, any of the above methods of treatment comprises the further step of co-administering to the patient one or more second therapeutic agents. The choice of second therapeutic agent may be made from any second therapeutic agent known to be useful for co-administration with apremilast. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

In particular, the combination therapies of this invention include co-administering a compound of Formula I, or a pharmaceutically acceptable salt thereof and a second therapeutic agent for treatment of the following conditions: psoriasis, including plaque-type psoriasis and refractory psoriasis; sarcoidosis, including cutaneous sarcoidosis; psoriatic arthritis; Behçet's Disease; prurigo nodularis; lupus, including cutaneous lupus; and uveitis.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a patient does not preclude the separate administration of that same therapeutic agent, any other second therapeutic agent or any compound of this invention to said patient at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula I or a pharmaceutical salt thereof alone or together with one or more of the above-described second therapeutic agents in the manufacture of a medicament, either as a single composition or as separate dosage forms, for treatment in a patient of a disease, disorder or symptom set forth above. Another aspect of the invention is a compound of Formula I or a pharmaceutical salt thereof for use in the treatment in a patient of a disease, disorder or symptom thereof delineated herein.

EXAMPLES

Example 1

Synthesis of (S)—N-(2-(1-d-2-(Methylsulfonyl)-1-(3-(ethoxy-d$_5$)-4-(methoxy-d$_3$)phenyl)ethyl)-1,3-dioxoisoindolin-4-yl)acetamide (Compound 113a)

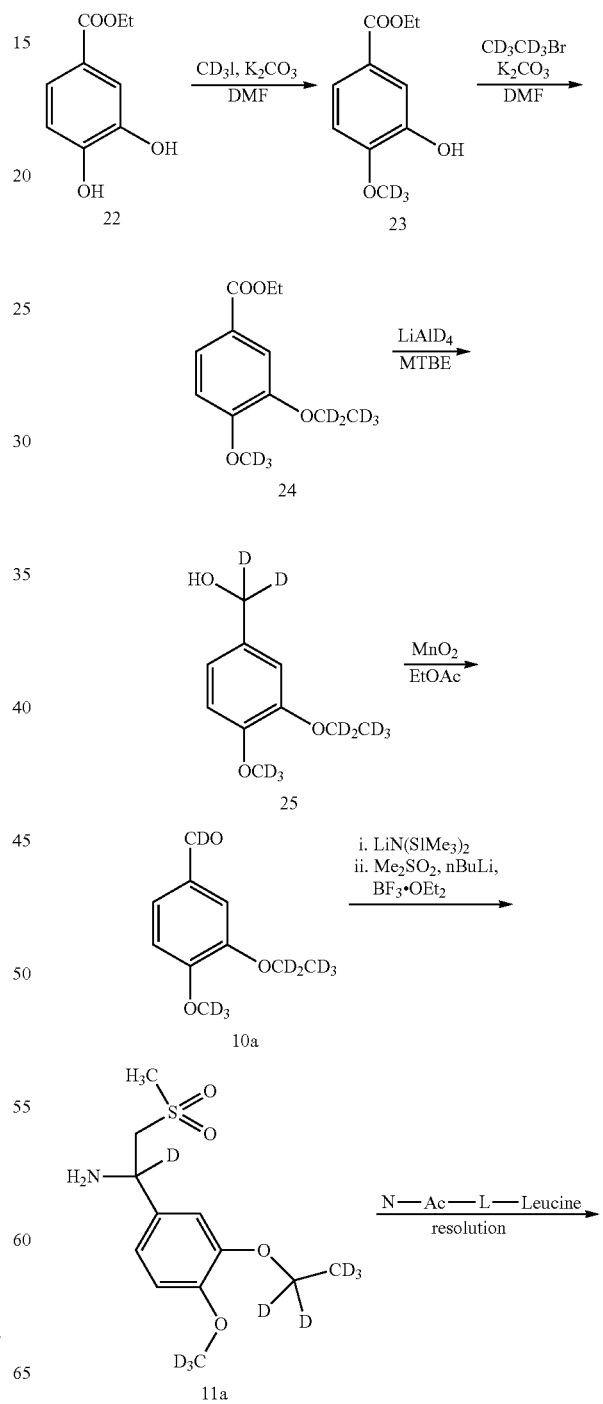

-continued

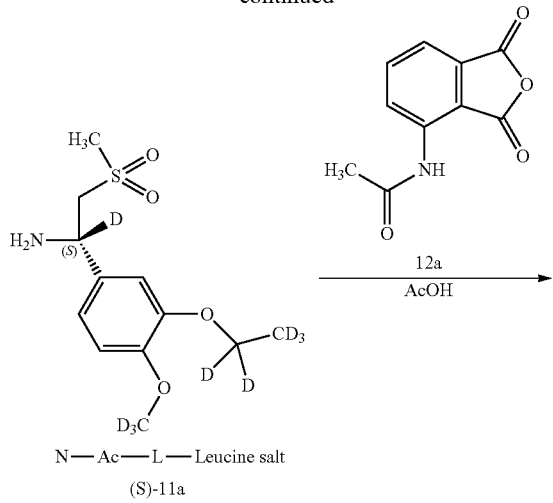

Step 1. Ethyl 3-hydroxy-4-(methoxy-d$_3$)-benzoate (23)

Commercially available ester 22 (10 g, 55 mmol) was mixed with CD$_3$I (99 atom % D, Cambridge Isotopes; 8.1 g, 55 mol) and K$_2$CO$_3$ (7.59 g) in DMF and stirred at room temperature over a weekend. LCMS showed three peaks with masses consistent with starting material (20%), the desired monoalkylated 23 (55%) product and the bisalkylated (23%) by-product. The reaction was filtered through a pad of Celite, washing with EtOAc, and the filtrate concentrated to almost dryness. The residue was dissolved in CH$_2$Cl$_2$ (300 mL) and the solution was washed with water (5×50 mL), brine, dried (Na$_2$SO$_4$) and concentrated. The crude product was purified by chromatography on silica gel eluting with EtOAc/heptane (1:9 to 1:6) then further triturated from heptane to give 4.1 g (36%) of the desired 23.

Step 2. Ethyl 3-(ethoxy-4)-4-(methoxy-d$_3$)-benzoate (24)

23 (4.1 g, 20 mmol) was dissolved in DMF (10 mL) and K$_2$CO$_3$ (2.5 g) and CD$_3$CD$_2$Br (99 atom % D, Cambridge Isotopes; 4.7 g, 41 mmol) were added. The reaction flask was sealed and stirred at room temperature for 24 hr. LCMS showed the reaction was complete. The mixture was filtered through a pad of Celite, washing with MTBE. The filtrate was concentrated to remove volatiles and water (100 mL) was added. The solids were collected under vacuum and washed with water (50 mL). The solid was re-dissolved in MTBE (200 mL) and the solution was washed with brine, dried (Na$_2$SO$_4$) and concentrated to give approximately 3.8 g (81%) of 24 (purity approximately 90% by LCMS).

Step 3. (3-(Ethoxy-d$_5$)-4-(methoxy-d$_3$)-phenyl)-1,1-d$_2$-methanol (25)

24 (3.8 g, 16.3 mmol) was dissolved in MTBE (50 mL) and LiAlD$_4$ (98 atom % D, Cambridge Isotopes; 0.7 g, 17 mmol) was added. The reaction mixture was stirred at room temperature overnight. LCMS indicated the reaction was complete. Aqueous NH$_4$Cl (20 mL) was added cautiously to quench the reaction and the mixture was filtered through a pad of Celite. The phases were separated and the aqueous phase was extracted with EtOAc (2×20 mL). The combined organic phases were dried (Na$_2$SO$_4$) and concentrated to give 2.8 g of 25 as a light yellow oil. This material was used directly in the next step.

Step 4. 3-(Ethoxy-d$_5$)-4-(methoxy-d$_3$)-benzaldehyde-d (10a)

25 (2.8 g, 16 mmol) was dissolved in EtOAc (30 mL). MnO$_2$ (14 g, 160 mmol) was added and the dark mixture was stirred at room temperature overnight. LCMS showed complete consumption of the starting material. The mixture was passed through a pad of Celite, washing with EtOAc, and the filtrate was concentrated to give a yellow oil. The oil was purified via chromatography on silica gel eluting with 20% EtOAc/heptane to give 2.05 g (68% for 2 steps) of 10a as a white solid.

Step 5. 1-(3-(Ethoxy-d$_5$)-4-(methoxy-d$_3$)-phenyl)-1-d-2-(methylsulfonyl)ethanamine (11a)

Methyl sulfone (1 g, 10.7 mmol) was suspended in THF (70 mL) and cooled in an acetone/dry ice bath to below −70° C. n-BuLi (2.5 M in hexanes, 4.6 mL, 11.5 mmol) was added and the mixture stirred 30 minutes. In a separate flask, a solution of 10a (1.9 g, 10.0 mmol) in THF (20 mL) was cooled to 0° C. Lithium hexamethyldisilazide (LHMDS) (1M in THF, 12 mL) was added. After 15 minutes boron trifluoride etherate (2.8 mL, 22 mmol) was added and stirring was continued for another 5 minutes. This solution was then added to the methyl sulfone/n-BuLi solution, with cooling in an acetone/thy ice bath to below −70° C. via a syringe. An exotherm was observed. This mixture was allowed to warm to room temperature and was stirred overnight. After cooling in an ice-water bath. K$_2$CO$_3$ (8 g) was added followed by water (50 mL). The layers were separated and the aqueous phase was extracted with EtOAc (2×20 mL). The combined organic solution was dried (Na$_2$SO$_4$) and concentrated to give a sticky oil. MTBE (30 mL) and aqueous HCl (4N, 30 mL) were added and the mixture stirred at room temperature for 2 hr to give a clear biphasic solution. The phases were separated and the organic solution extracted with aqueous HCl (4N, 25 mL). To the combined aqueous phases was added aqueous NaOH (24%) until pH>12. The aqueous phase was extracted with EtOAc (3×50 mL), the organic phases were dried (Na$_2$SO$_4$), and concentrated to give a yellow solid. The solid was suspended in MTBE (20 mL) and stirred for one hour. Filtration under vacuum gave 1.2 g (36%) of 11a.

Step 6. (S)-1-(3-(Ethoxy-d$_5$)-4-(methoxy-d$_3$)-phenyl)-1-d-2-(methylsulfonyl)ethanamine N-acetyl leucine salt ((S)-11a)

11a (1.2 g, 4.25 mmol) was mixed with N-acetyl-L-leucine (0.44 g, 2.55 mmol) in MeOH (10 mL). This mixture was heated at 70° C. for 3 hr then stirred at room temperature overnight. The solid was collected by vacuum filtration and suspended in MeOH (15 mL). The mixture was stirred at 70° C. for 2 hr, then at room temperature overnight. The solid was collected and the MeOH trituration was repeated. A 600-mg portion (31%) of (S)-11a was isolated with >99% ee.

Step 7. (S)—N-(2-(1-d-1-(3-(Ethoxy-$d_5$)-4-(methoxy-$d_3$)-phenyl)-2-(methylsulfonyl)ethyl)-1,3-dioxoisoindolin-4-yl)acetamide (Compound 113a)

(S)-11a (380 mg, 0.88 mmol) was mixed with known 12a (200 mg, 1 mmol; see US 20080234359) in acetic acid (6 mL) and heated at reflux for 24 hr to drive the reaction to completion. The mixture was concentrated and the colorless oil was re-dissolved in EtOAc (100 mL). The solution was washed with saturated aqueous NaHCO$_3$ (20 mL), dried (Na$_2$SO$_4$) and concentrated. The crude product was purified by column chromatography on an Analogix system eluting with 0-3% MeOH/CH$_2$Cl$_2$ to provide 360 mg (87%) of 113a. $^1$H-NMR (300 MHz, CDCl$_3$): δ 1.58 (s, 1H), 2.27 (s, 3H), 2.87 (s, 3H), 3.72 (d, J=14.3 1H), 4.55 (d, J=14.5, 1H), 6.84 (d, J=9.8, 1H). 7.11 (d, J=9.2, 2H). 7.49 (d, J=−6.5, 1H), 7.66 (s, 1H), 8.77 (d, J=7.7, 1H), 9.46 (s, 1H). $^{13}$C-NMR (75 MHz, CDCl$_3$): δ 24.97, 41.67, 54.47, 111.45, 112.38, 115.14, 118.25, 120.28, 124.99, 129.18, 131.07, 136.14, 137.66, 148.70, 167.51, 169.16. HPLC (method: 50 mm 3 µm Waters Atlantis T3 2.1 column gradient method 5-95% ACN+0.1% formic acid in 14 min with 4 min hold at 95% ACN+0.1% formic acid; wavelength: 305 nm): retention time: 5.96 min; 99.5% purity. MS (M+H): 470.3. Elemental Analysis (C$_{22}$H$_{15}$D$_9$N$_2$O$_7$S.H$_2$O): Calculated: C=54.20, H=5.38, N=5.75. Found: C=54.15, H=4.98, N=5.60.

Example 2

Synthesis of (S)—N-(2-(2-(Methylsulfonyl)-1-(3-(ethoxy-$d_5$)-4-(methoxy-$d_3$)phenyl)ethyl)-1,3-dioxoisoindolin-4-yl)acetamide (Compound 107a)

Scheme 5. Preparation of Compound 107a.

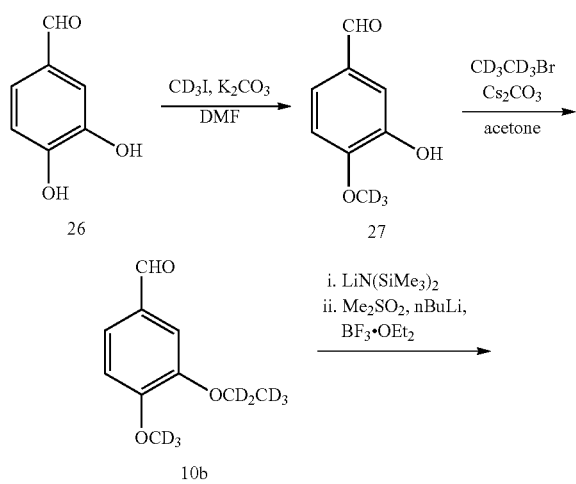

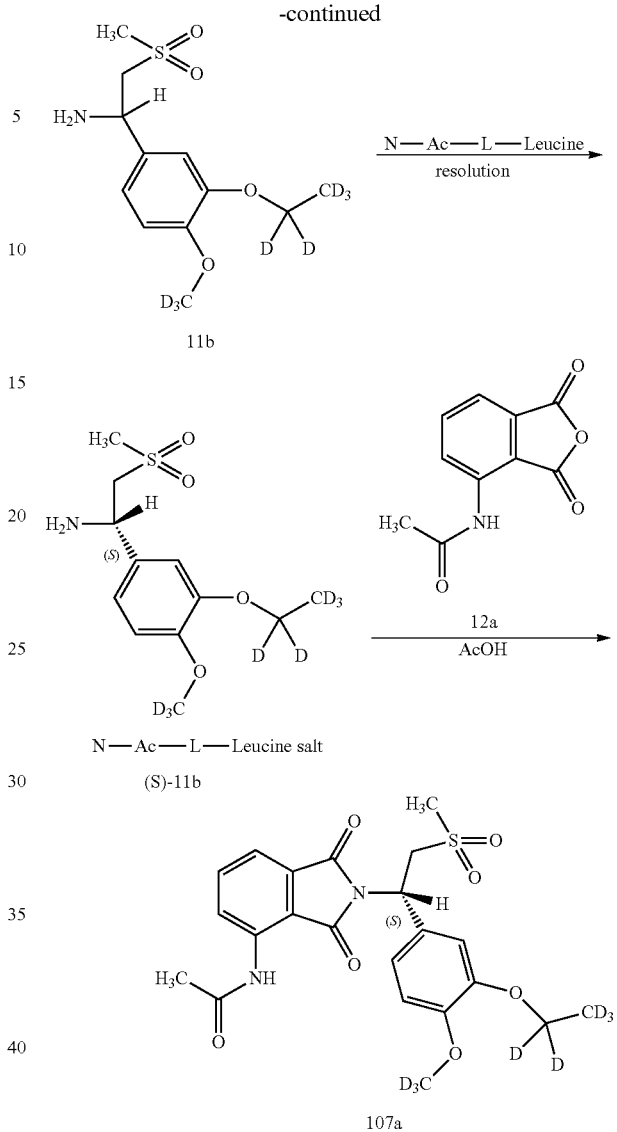

Step 1. 3-Hydroxy-4-(methoxy-$d_3$)-benzaldehyde (27)

Commercially available 3,4,-dihydroxy-benzaldehyde 26 (10 g, 80 mmol) was dissolved in DMF (50 mL). K$_2$CO$_3$ (10 g) was added and the solution was cooled in an ice-water bath. CD$_3$I (99 atom % D, Cambridge Isotopes; 12.4 g, 84 mmol) was slowly added, then the reaction was stirred at room temperature overnight. The reaction was diluted with EtOAc (200 mL) and filtered through a pad of Celite. The filtrate was concentrated to give a dark oil. EtOAc (150 mL) and water (50 mL) were added and the layers were separated. The aqueous phase was adjusted to pH 6 by the slow addition of 1N HCl and the mixture was extracted with EtOAc (2×100 mL). The combined organic solution was dried (Na$_2$SO$_4$) and concentrated. The crude material was purified by column chromatography on silica gel eluting with EtOAc/heptane (1:6 to 1:2) to give greater than 5 g of 27 of about 90% purity. This material was further, purified on an Analogix chromatography system eluting with 0-30% EtOAc/heptane to give 4.3 g (35%) of 27.

Step 2. 3-(Ethoxy-d$_5$)-4-(methoxy-d$_3$)-benzaldehyde (10b)

27 (4.3 g, 27.7 mmol) was mixed with Cs$_2$CO$_3$ (15 g, 46 mmol) in acetone and cooled in an ice-water bath. Bromoethane-d$_5$ (99 atom % D, Cambridge Isotopes; 3.8 g, 33.6 mmol) was added and the reaction was stirred overnight. MTBE was added and the mixture was filtered through a pad of Celite. After concentrating, the crude product was purified by chromatography on silica gel eluting with 1:4 EtOAc/heptane to give 2 g (38%) or the desired 10b.

Step 3. 1-(3-(Ethoxy-d$_5$)-4-(methoxy-d$_3$)-phenyl)-2-(methylsulfonyl)ethanamine (11b)

Methyl sulfone (1 g, 10.7 mmol) was suspended in THF (70 mL) and cooled in an acetone/dry ice bath to below −70° C. n-BuLi (2.5 M in hexanes, 4.8 mL, 11.9 mmol) was added and the mixture was stirred about 30 minutes. In a separate flask, a solution of the aldehyde 10b (2 g, 10.6 mmol) in THF (20 mL) was cooled to 0° C. LHMDS (1M in THF, 12 mL) was added. After 15 minutes boron trifluoride etherate (2.8 mL, 22 mmol) was added and stirring was continued for another 5 minutes. This solution was then added to the methyl sulfone/n-BuLi solution, with cooling in an acetone/dry ice bath at below −70° C., via a syringe. An exotherm was observed. This mixture was allowed to warm to room temperature and stirred overnight. After cooling in an ice-water bath, K$_2$CO$_3$ (8 g) was added followed by water (50 mL). The layers were separated and the aqueous phase was extracted with EtOAc (2×20 mL). The combined organic solution was dried (Na$_2$SO$_4$) and concentrated to give a sticky oil. MTBE (30 mL) and aqueous HCl (4N, 30 mL) were added and the mixture was stirred at room temperature for 2 hr to give a clear biphasic solution. The phases were separated and the organic phase was extracted with aqueous HCl (4 N, 25 mL). To the combined aqueous phases was added aqueous NaOH (24%) to raise the pH above 12. The solution was extracted with EtOAc (3×50 mL). The combined organic solution was dried (Na$_2$SO$_4$), and concentrated to give a yellow solid. The solid was suspended in MTBE (20 mL) and stirred for one hour. Filtration under vacuum gave 1.2 g (38%) of 11b as a light yellow solid.

Step 4. (S)-1-(3-(Ethoxy-d$_5$)-4-(methoxy-d$_3$)-phenyl)-2-(methylsulfonyl)ethanamine N-acetyl-L-leucine salt ((S)-11b)

11b (1.05 g, 3.73 mmol) was mixed with N-acetyl-L-leucine (0.39 g, 2.24 mmol) in MeOH (6 mL). This mixture was heated at 70° C. for 3 hr then stirred at room temperature overnight. The solid was collected by vacuum filtration and was suspended in MeOH (15 mL). The suspension was stirred at 70° C. for 2 hr then at room temperature overnight. The solid was collected and the MeOH trituration was repeated. A 400-mg portion (23%) of (S)-11b N-acetyl-L-leucine salt was obtained with >98% ee.

Step 5. (S)—N-(2-(1-(3-(Ethoxy-d$_5$)-4-(methoxy-d$_3$)-phenyl)-2-(methylsulfonyl)ethyl)-1,3-dioxoisoindolin-4-yl)acetamide (Compound 107a)

(S)-11b N-acetyl-L-leucine salt (220 mg, 0.5 mmol) was mixed with known 12a (123 mg, 0.6 mmol) in acetic acid (5 mL) and heated at reflux for 24 hr to drive the reaction to near completion. The mixture was concentrated, the colorless oil was dissolved in EtOAc (100 mL) and the solution was washed with saturated aqueous NaHCO$_3$ (20 mL). The organic phase was dried (Na$_2$SO$_4$) and concentrated. The crude product purified by column chromatography on an Analogix system eluting with 0-70% EtOAc/heptane to afford 210 mg (89%) of 107a. $^1$H-NMR (300 MHz, CDCl$_3$): δ 1.59 (s, 1H), 2.27 (s, 3H), 2.87 (s, 3H), 3.72 (dd, J=4.6, 14.4, 1H), 3.85 (s, 3H), 4.56 (dd, J=10.8, 14.4, 1H), 5.87 (dd, J=4.4, 10.6), 6.84 (d, J=8.8, 1H), 7.10 (d, J=7.0, 2H), 7.49 (d, J=6.6, 1H), 7.65 (t, J=7.3, 1H), 8.76 (d, J=8.0, 1H), 9.46 (s, 1H). $^{13}$C-NMR (75 MHz, CDCl$_3$): δ 24.97, 41.66, 48.60, 54.55, 55.96, 76.58, 77.01, 77.43, 111.48, 112.40, 115.14, 118.25, 120.29, 125.00, 129.26, 131.07, 136.14, 137.66, 148.70, 149.79, 167.51, 169.17, 169.53. HPLC (method: 50 mm 3 μm Waters Atlantis T3 2.1 column—gradient method 5-95% ACN+0.1% formic acid in 14 min with 4 min hold at 95% ACN+0.1% formic acid; wavelength: 305 nm): retention time: 6.02 min: >98.0% purity. Chiral HPLC (method: Chiralpak AD 25 cm column—isocratic method 78% hexane/22% isopropanol/0.01% diethylamine for 40 minutes at 1.00 mL/min; wavelength: 254 nm): retention time: 12.73 min (major enantiomer); >99% ee purity. MS (M+Na): 488.1. Elemental Analysis (C$_{22}$H$_{21}$D$_3$N$_2$O$_7$S): Calculated: C=56.76, H=5.20, N=6.02, S=6.89. Found: C=56.74, H=5.43, N=5.70, S=6.51.

Example 3

Synthesis of (S)—N-(2-(2-(Methylsulfonyl)-1-(3-ethoxy-4-methoxy-d$_3$)phenyl)ethyl)-1,3-dioxoisoindolin-4-yl)acetamide (Compound 114a)

Scheme 6. Preparation of Compound 114a.

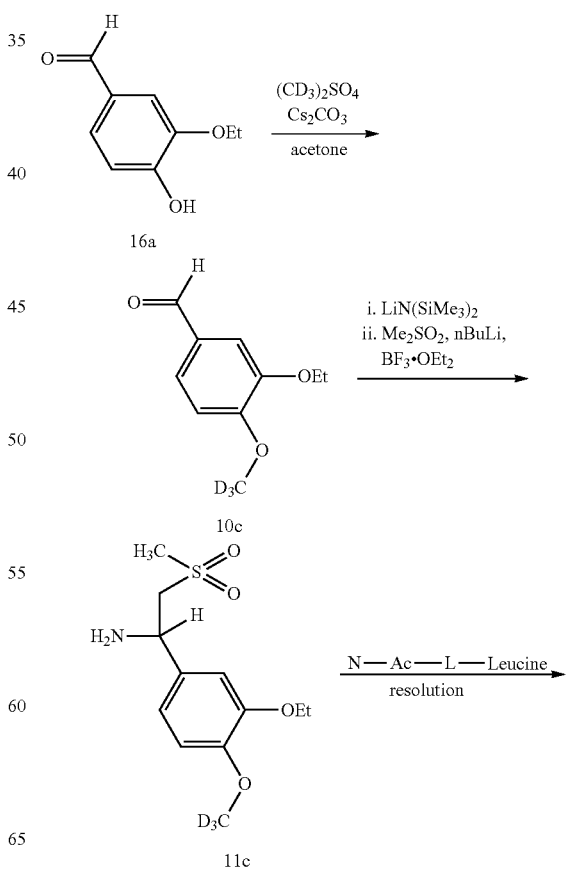

31

-continued

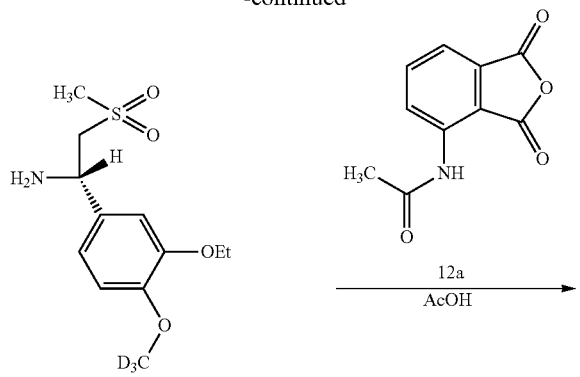

N—Ac—L—Leucine salt (S)-11c

114a

Step 1. 3-Ethoxy-4-(methoxy-d₃)-benzaldehyde (10c)

A mixture of commercially available 16a (5 g, 30 mmol) and Cs₂CO₃ (15 g, 46 mmol) in acetone was cooled in an ice-water bath. (CD₃)₂SO₄ (99 atom % D, Cambridge Isotopes; 2.7 mL, 30 mmol) was added and the reaction was allowed to warm slowly to room temperature and was stirred overnight. The mixture was filtered through a pad of Celite and concentrated to give 5.7 g (approx 100%) of 10c.

Step 2. 1-(3-Ethoxy-4-(methoxy-d₃)-phenyl)-2-(methylsulfonyl)ethanamine (11c)

Methyl sulfone (3 g, 32.1 mmol) was suspended in THF (280 mL) and cooled in an acetone/dry ice bath to below –70° C. n-BuLi (2.5 M in hexanes, 13.6 mL, 35.7 mmol) was added and the mixture was stirred about 30 minutes. In a separate flask a solution of 10c (5.7 g, 30.2 mmol) in THF (60 mL) was cooled to 0° C. LHMDS (0.1M in THF, 34.4 mL) was added. After 15 minutes boron trifluoride etherate (8 mL, 62.9 mmol) was added and the mixture was stirred for 5 minutes. This solution was added to the methyl sulfone/n-BuLi solution, with cooling in an acetone/dry ice bath to below –70° C. via a syringe. An exotherm was observed. This mixture Was allowed to warm to room temperature and was stirred overnight. After cooling in an ice-water bath, K₂CO₃ (24 g) was added followed by water (150 mL). The layers were separated and the aqueous phase was extracted with EtOAc (3×60 mL). The combined organic solution was dried (Na₂SO₄) and concentrated to give a sticky oil. MTBE (90 mL) and aqueous HO

32

(4N, 90 mL) were added to the residue and the mixture stirred at room temperature for 2 hr to give a clear biphasic solution. The phases were separated and die organic phase was extracted with aqueous HCl (4 N, 75 mL). To the combined aqueous phases was added aqueous NaOH (24%) to raise the pH above 12. The aqueous layer was extracted with EtOAc (3×150 mL). The combined organic solution was dried (Na₂SO₄) and concentrated to give a yellow solid. The solid was suspended in MTBE (60 mL) and stirred for one hour. Filtration under vacuum gave 2.7 g (31.4%) of 11c as a light yellow solid.

Step 3. (S)-1-(3-Ethoxy-4-(methoxy-d₃)-phenyl)-2-(methylsulfonyl)ethanamine N-acetyl-L-leucine salt ((S)-11c)

11c (2.3 g, 8.17 mmol) was mixed with N-acetyl-L-leucine (0.78 g, 4.48 mmol) in MeOH (12 mL). The mixture was heated at 70° C. for 3 hr then stirred at room temperature overnight. The solid was collected by vacuum filtration, suspended in MeOH (12 mL) and stirred at 70° C. for 2 hr, then at room temperature overnight. The solid was collected and the MeOH trituration was repeated. A 1-g portion (28.8%) of (S)-11c N-acetyl-L-leucine salt Was obtained with >98% ee.

Step 4. (S)—N-(2-(1-(3-Ethoxy-4-(methoxy-d₃)-phenyl)-2-(methylsulfonyl)ethyl)-1,3-dioxoisoindolin-4-yl)acetamide (114a)

(S)-11c (0.97 g, 2.2 mmol) was mixed with known 12a (470 mg, 2.5 mmol) in acetic acid (20 mL) and heated at reflux for 24 hr to drive the reaction to near completion. The mixture was concentrated, the colorless oil was dissolved in EtOAc (200 mL) and the solution was washed with saturated NaHCO₃ (40 mL). The organic phase was dried (Na₂SO₄) and concentrated. The crude product was purified by column chromatography on an Analogix system eluting with 0-70% EtOAc/heptane to afford 0.7 g (68%) of 114a. ¹H-NMR (300 MHz, CDCl₃): δ 1.47 (t, J=7.0, 3H), 1.61 (s, 1H), 2.26 (s, 3H), 2.87 (s, 3H), 3.72 (dd, J=4.6, 14.4, 1H), 4.11 (q, J=6.9, 14.0, 2H), 4.55 (dd, J=10.5, 14.4, 1H). 5.87 (dd, J=4.4, 10.6, 1H), 6.84 (d, J=8.7, 1H), 7.10 (d, J=6.5, 2H), 7.49 (d, J=7.3, 1H), 7.65 (t, J=7.7, 1H), 8.76 (d, J=8.5, 1H), 9.46 (s, 1H). ¹³C-NMR (75 MHz, CDCl₃): δ 14.70, 24.96, 41.65, 48.59, 54.54, 64.55, 111.46, 112.44, 115.14, 118.25, 120.32, 125.00, 129.24, 131.07, 136.14, 137.66, 148.67, 149.79, 167.51, 169.17, 169.53. HPLC (method: 50 min 3 μm Waters Atlantis T3 2.1 column—gradient method 5-95% ACN+0.1% formic acid in 14 min with 4 min hold at 95% ACN+0.1% formic acid; wavelength: 305 nm): retention time: 6.03 min; 97.4% purity. Chiral HPLC (method: Chiralpak AD 25 cm column—isocratic method 78% hexane/22% isopropanol/0.01% diethylamine for 40 minutes at 1.00 mL/min; wavelength: 254 nm): retention time: 12.69 min (major enantiomer); 39.03 min (minor enantiomer); >99% ee purity. MS (M+Na): 486.0. Elemental Analysis (C₂₂H₂₁D₃N₂O₇S): Calculated: C=57.01, H=5.22, N=6.04, S=6.92. Found: C=57.68, H=5.63, N=5.52, S=6.33.

Example 4

Synthesis of (S)—N-(2-(2-(Methylsulfonyl)-1-(3-(ethoxy-d$_5$)-4-(methoxy)phenyl)ethyl)-1,3-dioxoisoindolin-4-yl)acetamide (Compound 110a)

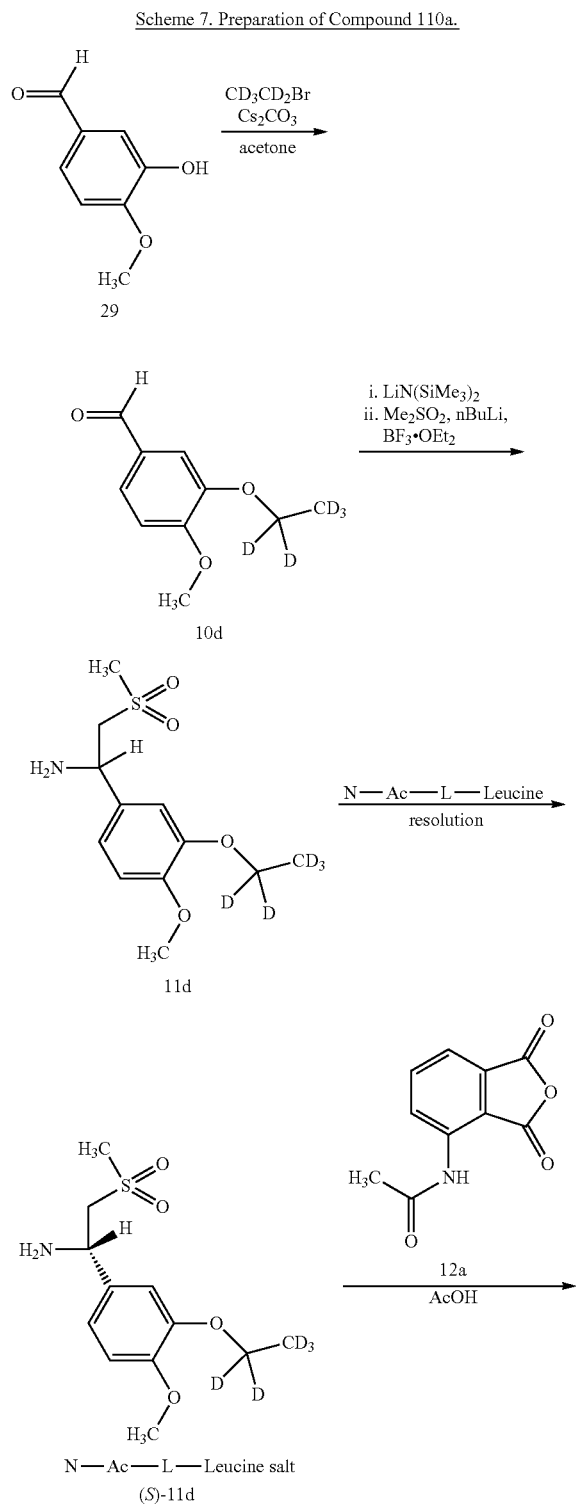

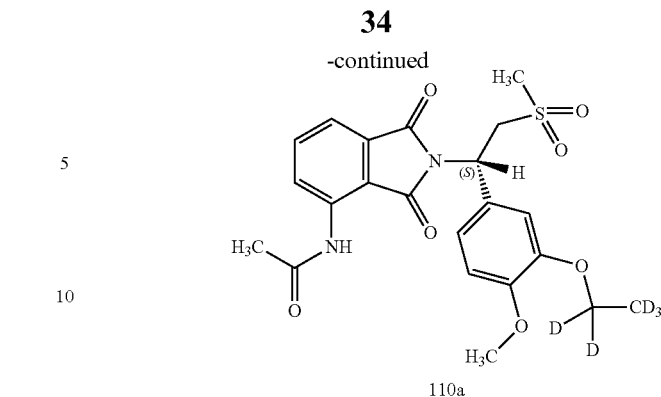

110a

Step 1. 3-(Ethoxy-d$_5$)-4-methoxy-benzaldehyde (10d)

Commercially available 2.9 (5 g, 30 mmol) was mixed with Cs$_2$CO$_3$ (15 g, 46 mmol) in acetone and cooled in an ice-water bath. Bromoethane-d$_5$ (99 atom % D, Cambridge Isotopes; 3.8 g, 33.6 mmol) was added and the reaction was allowed to warm slowly to room temperature and was stirred overnight. The reaction was diluted with MTBE, filtered through a pad of Celite, and concentrated to give 5.5 g (approx 100%) of 10d.

Step 2. 1-(3-(Ethoxy-d$_5$)-4-methoxy-phenyl)-2-(methylsulfonyl)ethanamine (11d)

Methyl sulfone (2.76 g, 29.5 mmol) was suspended in THF (250 mL) and cooled in an acetone/dry ice bath to below −70° C. n-BuLi (2.5 M in hexanes, 12.5 mL, 31 mmol) was added and the mixture was stirred for about 30 minutes. In a separate flask a solution of the aldehyde 10d (5.25 g, 27.6 mmol) in THF (50 mL) was cooled to 0° C. LHMDS (1M in THF, 31.7 mL) was added. After 15 minutes boron trifluoride etherate (7.36 mL, 57.8 mmol) was added and the mixture was stirred another 5 minutes. This solution was then added to the methyl sulfone/n-BuLi solution, with cooling in an acetone/dry ice bath at below −70° C., via a syringe. An exotherm was observed. This mixture was allowed to warm to room temperature and was stirred overnight. After cooling in an ice-water bath, K$_2$CO$_3$ (24 g) was added followed by water (150 mL). The layers were separated and the aqueous phase was extracted with EtOAc (3×60 mL). The combined organic solution was dried (Na$_2$SO$_4$) and concentrated to give a sticky oil. MTBE (90 mL) and aqueous HCl (4N, 90 mL) were added and the mixture was stirred at room temperature for 2 hr to give a clear biphasic solution. The phases were separated and the organic phase was extracted with aqueous HCl (4 N, 75 mL). To the combined aqueous phases was added aqueous NaOH (24%) to raise the pH above 12. The mixture was extracted with EtOAc (3×150 mL). The combined organic solution was dried (Na$_2$SO$_4$), and concentrated to give a yellow solid. The solid was suspended in MTBE (60 mL) and stirred for one hour. Filtration under vacuum afforded 2.7 g (34.2%) of 11d as a light yellow solid.

Step 3. ((S)-1-(3-(Ethoxy-d$_5$)-4-methoxy-phenyl)-2-(methylsulfonyl)ethanamine N-acetyl L-leucine salt ((S)-11d)

11d (2.6 g, 9.33 mmol) was mixed with N-acetyl-L-leucine (0.98 g, 5.6 mmol) in MeOH (15 mL). This mixture was heated at 70° C. for 3 hr then stirred at room temperature overnight. The solid was collected by vacuum filtration and suspended in WON (15 mL). The suspension was stirred at 70° C. for 2 hr then at room temperature overnight. The solid was collected and the MeOH trituration was repeated. A 1-g portion (23%) of (S)-11d N-acetyl-L-leucine salt was obtained with >98% ee.

Step 4. (S)—N-(2-(1-(3-(Ethoxy-d₅)-4-methoxyphenyl)-2-(methylsulfonyl)ethyl)-1,3-dioxoisoindolin-4-yl)acetamide (110a)

(S)-11d (1.4 g, 3.2 mmol) was mixed with known 12a (0.77 g, 3.84 mmol) in acetic acid (20 mL) and heated at reflux for 24 hr to drive the reaction to near completion. The mixture was concentrated, the colorless oil was dissolved in EtOAc (200 mL) and the solution was washed with saturated NaHCO₃ (40 mL). The organic layer was dried (Na₂SO₄) and concentrated. The crude product was purified by column chromatography on an Analogix system eluting with 0-70% EtOAc/heptane (in 1 hr) to afford 1.2 g (80%) of 110a. ¹H-NMR (300 MHz, CDCl₃): δ 1.59 (s, 1H), 2.27 (s, 3H), 2.87 (s, 3H), 3.72 (dd, J=4.6, 14.4, 1H), 3.85 (s, 3H), 4.56 (dd, J=10.8, 14.4, 1H), 5.87 (dd, J=4.4, 10.6), 6.84 (d, J=8.8, 1H), 7.10 (d, J=7.0, 2H), 7.49 (d, J=6.6, 1H), 7.65 (t, J=7.3, 1H), 8.76 (d, J=8.0, 1H), 9.46 (s, 1H). ¹³C-NMR (75 MHz, CDCl₃): δ 24.97, 41.66, 48.60, 54.55, 55.96, 76.58, 77.01, 77.43, 111.48, 112.40, 115.14, 118.25, 120.29, 125.00, 129.26, 131.07, 136.14, 137.66, 148.70, 149.79, 167.51, 169.17, 169.53. HPLC (method: 50 mm 3 μm Waters Atlantis T3 2.1 column—gradient method 5-95% ACN+0.1% formic acid in 14 min with 4 min hold at 95% ACN+0.1% formic acid; wavelength: 305 nm): retention time: 6.02 min; >98.0% purity. Chiral HPLC (method: Chiralpak AD 25 cm column—isocratic method 78% hexane/22% isopropanol/0.01% diethylamine for 40 minutes at 1.00 mL/min; wavelength: 254 nm): retention time: 12.73 min (major enantiomer); >99% ee purity. MS (M+Na): 488.1. Elemental Analysis (C₂₂H₂₁D₃N₂O₇S): Calculated: C=56.76, H=5.20, N=6.02, S=6.89. Found: C=56.74, H=5.43, N=5.70, S=6.51.

Example 5

Synthesis of Intermediate 12b

Scheme 8. Preparation of 12b.

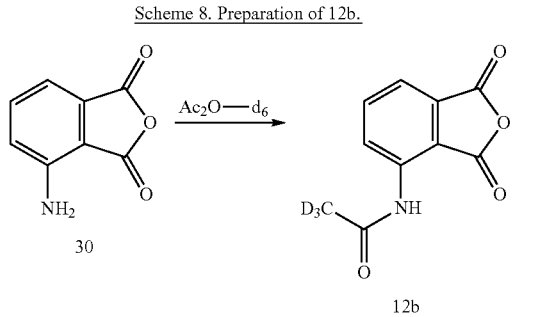

N-(1,3-dioxo-1,3-dihydroisobenzofuran-4-yl)acetamide-d3 (12b)

Commercially available 4-aminoisobenzofuran-1,3-dione 30 (5 g, 30.6 mmol) was suspended in acetic anhydride-d₆ (98 atom % D, Cambridge Isotopes; 10 g) and heated at reflux for 3 hr, then stirred at room temperature overnight. The solution was cooled to 0° C. and filtered, then the solid was washed with MTBE and dried to provide 2.5 g of 12b.

Example 6

Synthesis of (S)—N-(2-(1-(3-(Ethoxy-d₅)-4-(methoxy-d₃)-phenyl)-2-(methylsulfonyl)ethyl)-1,3-dioxoisoindolin-4-yl)acet-d₃-amide (Compound 115a)

Scheme 8. Preparation of 115a.

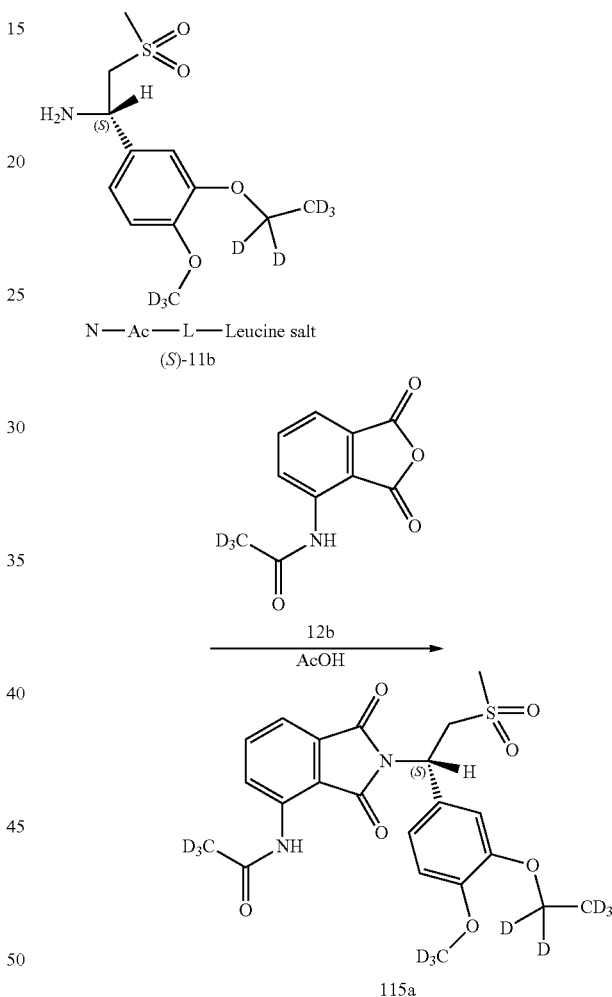

(S)—N-(2-(1-(3-(Ethoxy-d₅)-4-methoxy-d₃)-phenyl-2-(methylsulfonyl)ethyl)-1,3-dioxoisoindolin-4-yl) acet-d₃-amide (115a)

(S)-11b N-acetyl-L-leucine salt (200 mg, 0.44 mmol; see Scheme 5) was mixed with 12b (130 mg; see Scheme 8) in acetic acid (5 mL) and the solution was heated at 80° C. for 20 hr. The mixture was concentrated and the colorless oil was re-dissolved in EtOAc (100 mL). The solution was washed with saturated aqueous NaHCO₃ (20 mL), dried (Na₂SO₄) and concentrated. The crude product was purified by column chromatography on an Analogix system eluting with 0-70% EtOAc/heptane to provide 174 mg (73%) of 115a. ¹H-NMR (300 MHz, CDCl$_3$): δ 1.55 (s, 1H), 2.87 (s, 3H), 3.72 (dd, J=4.4, 14.3, 1H), 4.56 (dd, J=10.5, 14.4, 1H), 5.87 (dd, J=4.4, 10.5, 1H), 6.84 (d, J=8.5, 1H), 7.10 (d, j=7.0, 2H), 7.49 (d, J=7.3, 1H), 7.66 (t, J=7.5, 1H), 8.76 (d, J=8.3, 1H), 9.46 (s, 1H). $^{13}$C-NMR (75 MHz, CDCl$_3$): δ 41.66, 48.61, 54.56, 76.58, 77.00, 77.21, 77.43, 111.45, 112.40, 115.14, 118.26, 120.29, 125.01, 129.24, 131.07, 136.15, 137.66, 148.70, 167.52, 169.54. HPLC (method: 50 mm 3 μm Waters Atlantis T3 2.1 column—gradient method 5-95% ACN+0.1% formic acid in 14 min with 4 min hold at 95% ACN+0.1% formic acid; wavelength: 305 nm): retention time: 5.96 min; 99.1% purity. MS (M+H): 472.0. Elemental Analysis (C$_{22}$H$_{16}$D$_8$N$_2$O$_7$S): Calculated: C=56.04, H=5.13, N=5.94. Found: C=55.90, H=5.23, N=5.85.

Example 7

(S)—N-(2-(1-(3-(Ethoxy-d$_5$)-4-(methoxy-d$_3$)-phenyl)-2-((methyl-d$_3$)-sulfonyl)-2,2-d$_2$-ethyl)-1,3-dioxoisoindolin-4-yl)acetamide (Compound 116a)

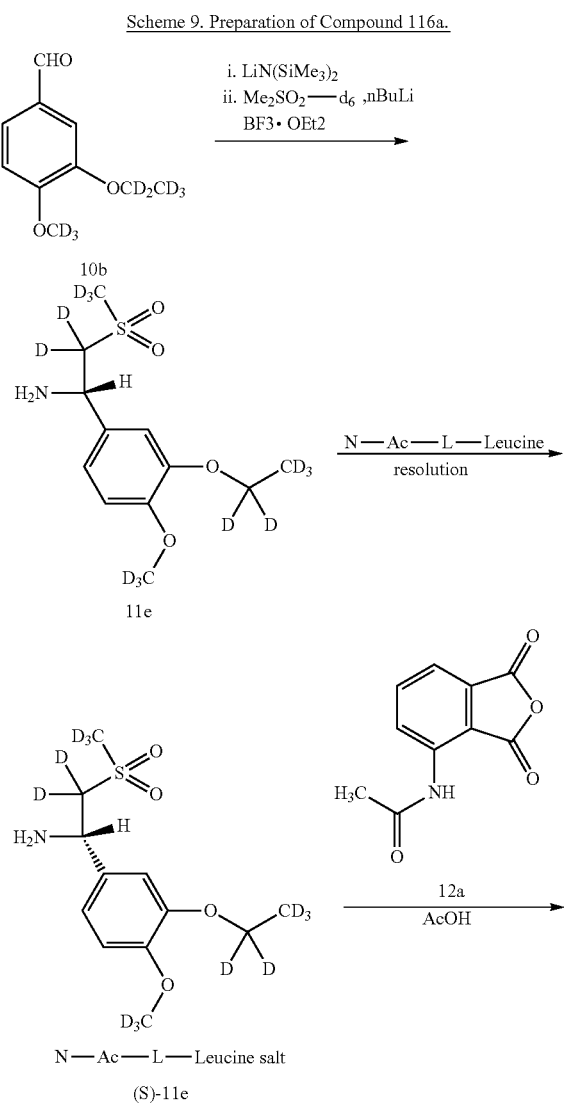

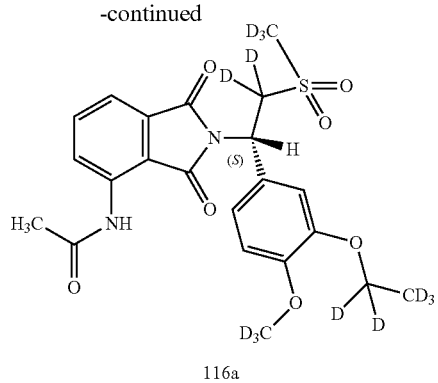

Step 1. 1-(3-(Ethoxy-d$_5$)-4-(methoxy-d$_3$)-phenyl)-2-((methyl-d$_3$)-sulfonyl)-2,2-d$_2$-ethanamine (11e)

Methyl sulfone-d$_6$ (99 atom % D, Isotec; 1 g, 10.0 mmol) was suspended in THF (70 mL) and cooled in an acetone/dry ice bath to below −70° C. n-BuLi (2.5 M in hexanes, 4.4 mL, 11 mmol) was added and the mixture was stirred about 30 minutes. In a separate flask, a solution of the aldehyde 10b (1.91 g, 10.0 mmol; see Scheme 5) in THF (20 mL) was cooled to 0° C. LHMDS (1M in THF, 11 mL) was added. After 15 minutes boron trifluoride etherate (2.8 mL, 22 mmol) was added and stirring was continued for another 5 minutes. This solution was added to the methyl sulfone-d$_6$/n-BuLi solution, with cooling in an acetone/dry ice bath to below −70° C., via a syringe. An exotherm was observed. The mixture was allowed to warm to room temperature and was stirred overnight. After cooling in an ice-water bath, K$_2$CO$_3$ (8 g) was added followed by water (50 mL). The layers were separated and the aqueous phase was extracted with EtOAc (2×20 mL). The combined organic solution was dried (Na$_2$SO$_4$) and concentrated to give a sticky oil. MTBE (30 mL) and aqueous HCl (4N, 30 mL) were added and the mixture was stirred at room temperature for 2 hr to give a clear biphasic solution. The phases were separated and the organic phase was extracted with aqueous HCl (4 N, 25 mL). To the combined aqueous phases was added aqueous NaOH (24%) to raise the pH above 12. The solution was extracted with EtOAc (3×50 mL). The combined organic solution was dried (Na$_2$SO$_4$), and concentrated to give a yellow solid. The solid was suspended in MTBE (20 mL) and stirred for one hour. Filtration under vacuum gave 1.2 g (37%) or 11e as a light yellow solid.

$^1$H NMR and LCMS showed some loss of isotopic purity alpha to the sulfone. This D-to-H exchange likely occurred during the acid/base extraction. Use of deuterated solvents is preferred throughout the workup.

The less isotopically pure material was dissolved in MeOD (99 atom % D, Cambridge Isotopes; 30 mL) and K$_2$CO$_3$ (0.5 g) was added. This mixture was heated at 70° C. for 6 hr and then concentrated to dryness. Fresh MeOD (30 mL) was added and the mixture heated to 70° C. overnight. The cooled solution was diluted with EtOAc (100 mL) and the mixture was filtered. The filtrate was concentrated and re-dissolved in EtOAc (100 mL). The solution was washed with D$_2$O (99.9 atom % D, Cambridge isotopes; 20 mL). The organic phase was dried (Na$_2$SO$_4$) and concentrated to give approximately 1 g of 11e with high isotopic purity restored.

Step 2. (S)-1-(3-(Ethoxy-d₅)-4-(methoxy-d₃)-phenyl)-2-((methyl-d₃)-sulfonyl)-2,2-d₂-ethanamine N-acetyl-L-leucine salt ((S)-11e)

11e (630 mg, 2.2 mmol) was mixed with N-acetyl-L-leucine (0.23 g, 1.32 mmol) in MeOD (99 atom % D, Cambridge Isotopes; 6 mL). This mixture was heated at 70° C. for 3 hr then stirred at room temperature overnight. The solid was collected by vacuum Filtration and suspended in MeOH (6 mL). The mixture was stirred at 70° C. for 2 hr then at room temperature overnight. The solid was collected and the MeOH trituration was repeated. A 300-mg portion (29%) of (S)-11e N-acetyl-L-leucine salt was obtained with >99% ee.

Step 3. (S)—N-(2-(1-(3-d₅)-4-(methoxy-d₃)-phenyl)-2-((methyl-d₃)-sulfonyl)-2,2-d₂-ethyl)-1,3-dioxoisoindolin-4-yl)acetamide (116a)

(S)-11e N-acetyl-L-leucine salt (280 mg, 0.62 mmol) was mixed with known 12a (145 mg, 0.7 mmol) in acetic acid-d (99 atom % D, Aldrich; 5 mL) and heated to reflux for 24 hr to drive the reaction to near completion. The mixture was concentrated and the colorless oil was dissolved in EtOAc (100 mL). The solution was washed with NaHCO₃ (20 mL), dried (Na₂SO₄) and concentrated. The crude product was purified by column chromatography on an Analogix system eluting with 0-3% MeOH/CH₂Cl₂ to provide 245 mg (84%) of 116a. ¹H-NMR (300 MHz, CDCl₃): δ 1.57 (s, 1H), 2.26 (s, 3H), 5.86 (s, 1H), 6.84 (d, J=6.8, 1H), 7.10 (d, J=6.8, 2H), 7.49 (d, J=6.4, 1H), 7.65 (t, J=7.9, 1H), 8.76 (d, J=8.5, 1H), 9.46 (s, 1H). ¹³C-NMR (75 MHz, CDCl₃): δ 24.97, 48.43, 111.45, 112.40, 115.14, 118.25, 120.28, 125.00, 129.22, 131.07, 136.14, 137.66, 148.70, 149.79, 167.52, 169.17, 169.54. HPLC (method: 50 mm 3 μm Waters Atlantis T3 2.1 column—gradient method 5-95% ACN+0.1% formic acid in 14 min with 4 min hold at 95% ACN+0.1% formic acid; wavelength: 305 nm): retention time: 5.97 min; 99.7% purity. MS (M+H): 474.3. Elemental Analysis ($C_{22}H_{11}D_{13}N_2O_7S$): Calculated: C=55.80, H=5.11, N=5.92. Found: C=52.73, H=4.73, N=5.43.

Example

Evaluation of Metabolic Stability

Microsomal Assay:
Human liver microsomes (20 mg/mL) are obtained from Xenotech, LLC (Lenexa, Kans.). β-nicotinamide adenine dinucleotide phosphate, reduced form (NADPH), magnesium chloride (MgCl₂), and dimethyl sulfoxide (DMSO) are purchased from Sigma-Aldrich.

Determination of Metabolic Stability:
7.5 mM stock solutions of test compounds are prepared in DMSO. The 7.5 mM stock solutions are diluted to 12.5-50 μM in acetonitrile (ACN). The 20 mg/mL, human liver microsomes are diluted to 0.625 mg/ml, in 0.1 M potassium phosphate buffer, pH 7.4, containing 3 mM MgCl₂. The diluted microsomes are added to wells of a 96-well deep-well polypropylene plate in triplicate. A 10 μL aliquot of the 12.5-50 μM test compound is added to the microsomes and the mixture is pre-warmed for 10 minutes. Reactions are initiated by addition of pre-warmed NADPH solution. The final reaction volume is 0.5 mL and contains 0.5 mg/mL human liver microsomes, 0.25-1.0 μM test compound, and 2 mM NADPH in 0.1 M potassium phosphate butler, pH 7.4, and 3 mM MgCl₂. The reaction mixtures are incubated at 37° C., and 50 μL aliquots are removed at 0, 5, 10, 20, and 30 minutes and added to shallow-well 96-well plates which contain 50 μL of ice-cold ACN with internal standard to stop the reactions. The plates are stored at 4° C. for 20 minutes after which 100 μL of water is added to the wells of the plate before centrifugation to pellet precipitated proteins. Supernatants are transferred to another 96-well plate and analyzed for amounts of parent remaining by LC-MS/MS using an Applied Bio-systems API 4000 mass spectrometer. The same procedure is followed for apremilast and the positive control, 7-ethoxycoumarin (1 μM). Testing is done in triplicate.

Data Analysis:
The in vitro $t_{1/2}$s for test compounds are calculated from the slopes of the linear regression of % parent remaining (ln) vs incubation time relationship.

in vitro $t_{1/2}=0.693/k$ $k=-$[slope of linear regression of % parent remaining (ln) vs incubation time]

Data analysis is performed using Microsoft Excel Software.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention.

What is claimed is:
1. A method of inhibiting PDE4 in a subject in need thereof, comprising administering to the subject an effective amount of a compound of Formula I:

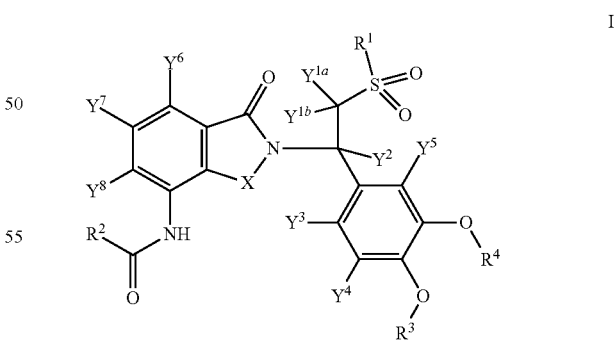

or a pharmaceutically acceptable salt thereof, wherein:
$R^1$ is selected from $CH_3$, $CH_2D$, $CHD_2$, and $CD_3$;
$R^2$ is methyl or $CD_3$;
$R^3$ is $CD_3$;
$R^4$ is an ethyl group substituted with zero to five deuterium, or is a cyclopentyl group substituted with zero to nine deuterium;

X is C=O;
each of $Y^{1a}, Y^{1b}, Y^2, Y^3, Y^4, Y^5, Y^7$ and $Y^8$ is independently selected from H and D; and
$Y^6$ is selected from Cl, H, and D.

2. A method of reducing TNF-α levels in a subject in need thereof, comprising administering to the subject an effective amount of a compound Formula I:

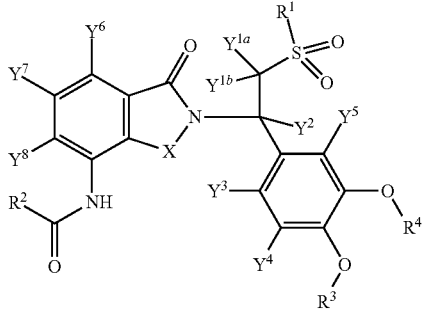

or a pharmaceutically acceptable salt thereof, wherein:
$R^1$ is selected from $CH_3$, $CH_2D$, $CHD_2$, and $CD_3$;
$R^2$ is methyl or $CD_3$;
$R^3$ is $CD_3$;
$R^4$ is an ethyl group substituted with zero to five deuterium, or is a cyclopentyl group substituted with zero to nine deuterium;
X is C=O;
each of $Y^{1a}, Y^{1b}, Y^2, Y^3, Y^4, Y^5, Y^7$ and $Y^8$ is independently selected from H and D; and
$Y^6$ is selected from Cl, H, and D.

3. A method of treating a disease selected from the group consisting of in a patient in need thereof comprising administering to the patient an effective amount of a compound of Formula I:

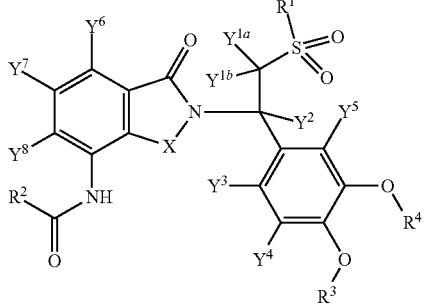

or a pharmaceutically acceptable salt thereof, wherein:
$R^1$ is selected from $CH_3$, $CH_2D$, $CHD_2$, and $CD_3$;
$R^2$ is methyl or $CD_3$;
$R^3$ is $CD_3$;
$R^4$ is an ethyl group substituted with zero to five deuterium, or is a cyclopentyl group substituted with zero to nine deuterium;
X is C=O;
each of $Y^{1a}, Y^{1b}, Y^2, Y^3, Y^4, Y^5, Y^7$ and $Y^8$ is independently selected from H and D; and
$Y^6$ is selected from Cl, H, and D.

4. The method of claim 3, wherein the condition is sarcoidosis.

5. The method of claim 4, wherein sarcoidosis is cutaneous sarcoidosis.

6. The method of claim 3, wherein lupus is cutaneous lupus.

7. The method of claim 3, wherein the disease is selected from Behçet's Disease and rheumatoid arthritis.

8. The method of claim 3, wherein the compound of Formula I has predominantly the (S) configuration at the carbon attached to $Y^2$ and is represented by the following Formula Ia:

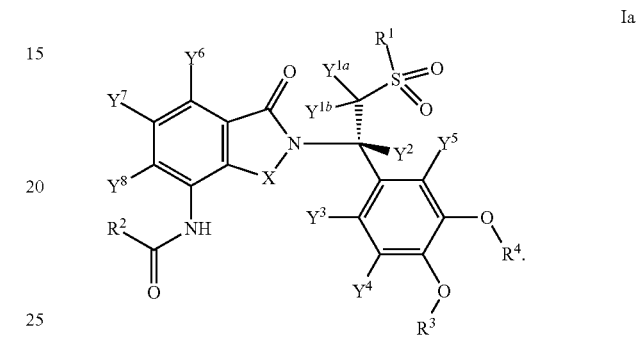

9. The method of claim 3, wherein $Y^6$, $Y^7$ and $Y^8$ are the same.

10. The method of claim 3, wherein $Y^{1a}$ and $Y^{1b}$ are the same.

11. The method of claim 3, wherein $Y^3$, $Y^4$ and $Y^5$ are the same.

12. The method of claim 3, wherein $R^1$ is $CH_3$ or $CD_3$.

13. The method of claim 3, wherein $R^4$ is $CD_2CD_3$.

14. The method of claim 8, wherein $Y^6$, $Y^7$ and $Y^8$ are the same.

15. The method of claim 8, wherein $Y^{1a}$ and $Y^{1b}$ are the same.

16. The method of claim 8, wherein $Y^3$, $Y^4$ and $Y^5$ are the same.

17. The method of claim 8, wherein $R^1$ is $CH_3$ or $CD_3$.

18. The method of claim 8, wherein $R^4$ is $CD_2CD_3$.

19. The method of claim 3, wherein the compound is selected from the group consisting of Compound 100

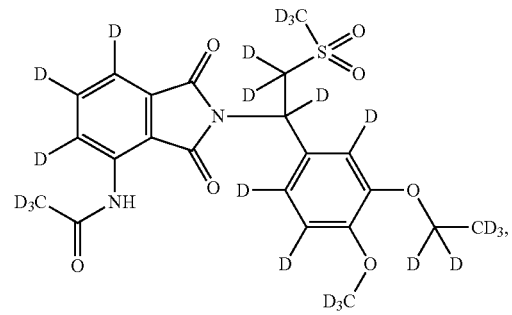

Compound 101
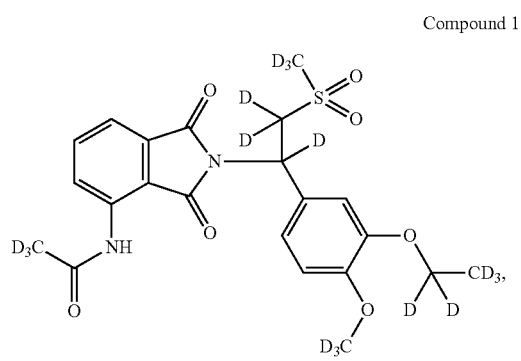
Compound 105
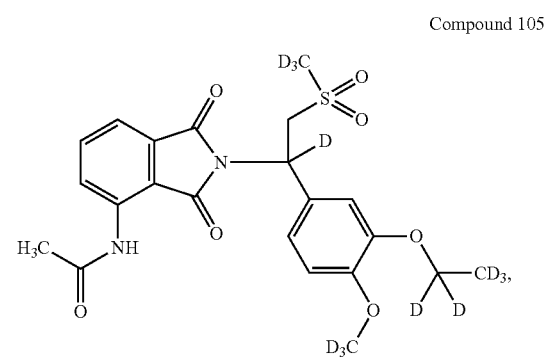
Compound 102
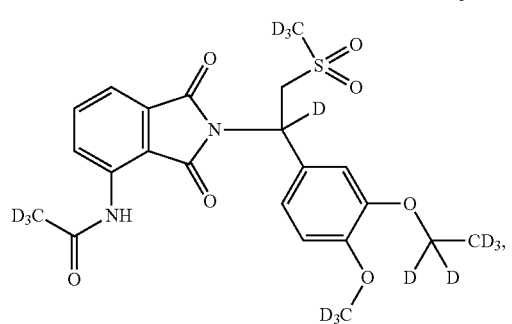
Compound 106
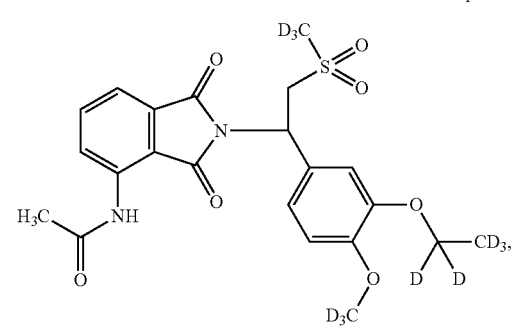
Compound 103
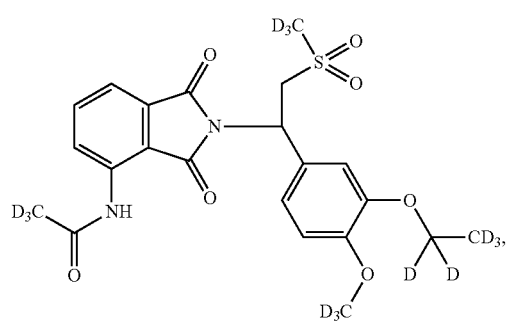
Compound 107
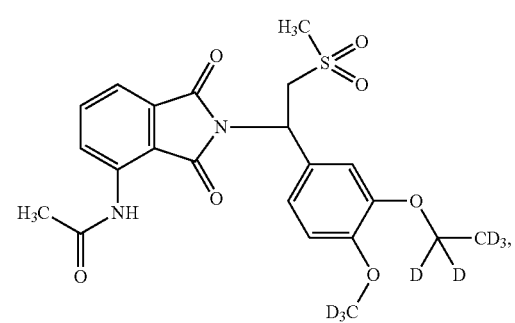
Compound 104
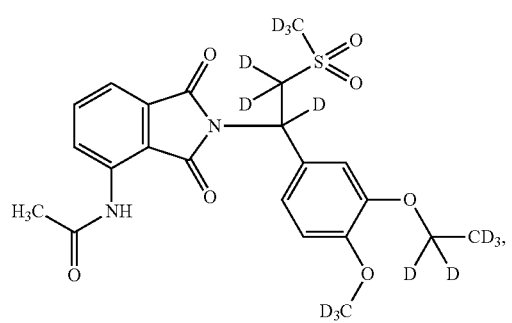
Compound 108
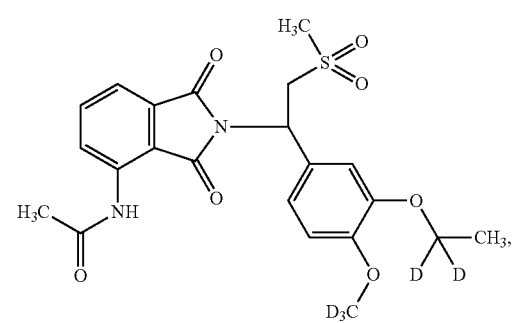

-continued
Compound 109
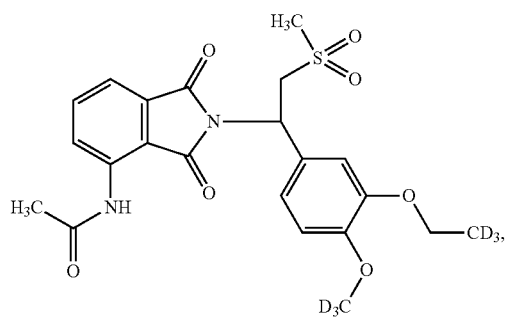
Compound 110
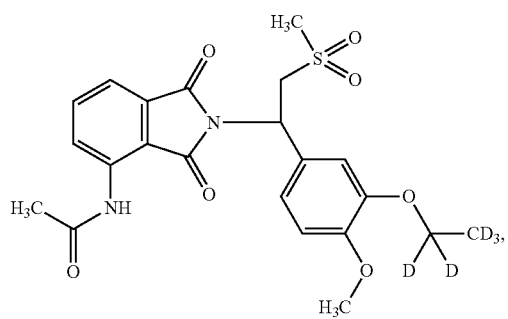
Compound 111
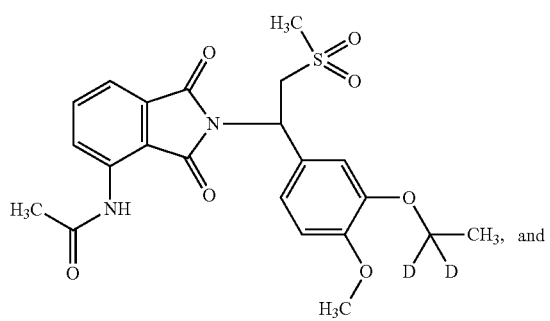
and
Compound 112
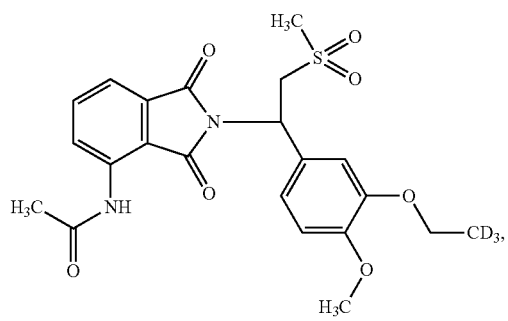
or a pharmaceutically acceptable salt of any of the foregoing.
20. The method of claim 8, wherein the compound is selected from the group consisting of
Compound 107a
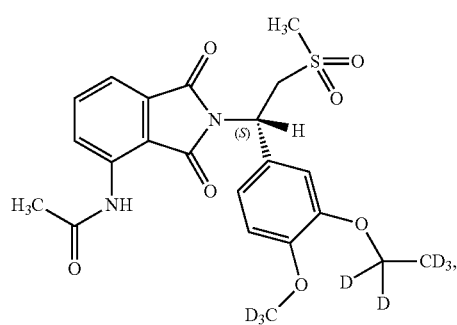
Compound 110a
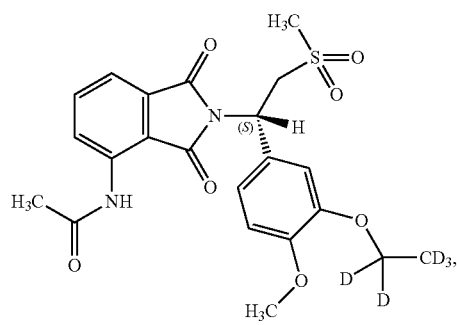
Compound 113a
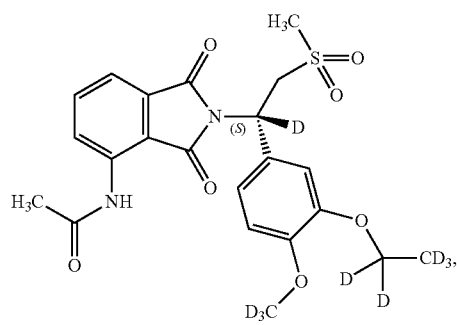
Compound 114a
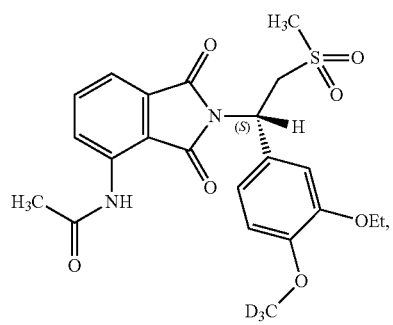

Compound 115a
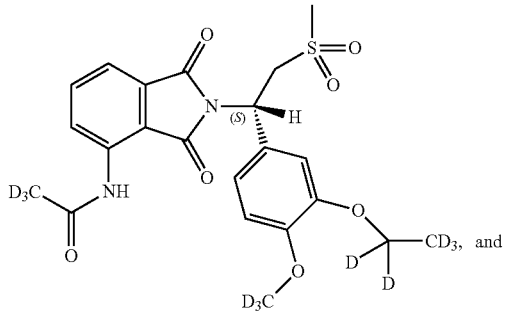
Compound 116a
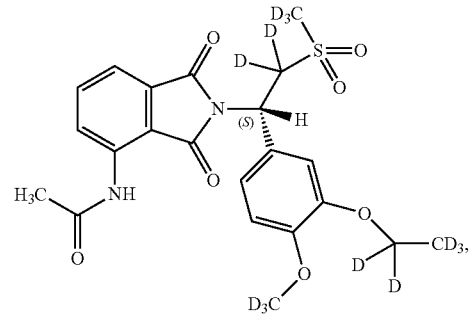
or a pharmaceutically acceptable salt of any of the foregoing.
21. The method of claim 3 wherein any atom not designated as deuterium is present at its natural isotopic abundance.
* * * * *

UNITED STATES PATENT AND TRADEMARK OFFICE
CERTIFICATE OF CORRECTION

PATENT NO. : 8,404,737 B2
APPLICATION NO. : 13/364724
DATED : March 26, 2013
INVENTOR(S) : Liu It is certified that error appears in the above-identified patent and that said Letters Patent is hereby corrected as shown below:

In the Claims

Column 41, Line 7, Claim 1    replace the phrase "amount of a compound Formula I" with "amount of a compound of Formula I"

Column 41, Line 36, Claim 3    insert --sarcoidosis, Behçet's Disease, prurigo nodularis, lupus, rheumatoid arthritis, and rheumatoid spondylitis-- between the phrases "consisting of" and "in a patient in need thereof"

Signed and Sealed this
Twenty-second Day of October, 2013

Teresa Stanek Rea
*Deputy Director of the United States Patent and Trademark Office*